United States Patent
Sung et al.

(10) Patent No.: US 7,351,421 B2
(45) Date of Patent: *Apr. 1, 2008

(54) DRUG-ELUTING STENT HAVING COLLAGEN DRUG CARRIER CHEMICALLY TREATED WITH GENIPIN

(76) Inventors: Hsing-Wen Sung, 7 F, No. 15, Alley 7, Lane 298, Sec. 2, Kung-Fu Road, Hsinchu (TW) 300; Mei-Chin Chen, 10 F, No. 4, Gueiyang St., Taishan Shiang (TW) 243; Peter Y Tu, 5061 Barkwood Avenue, Irvine, CA (US) 92604; Hosheng Tu, 15 Riez, Newport Beach, CA (US) 92657

( * ) Notice: Subject to any disclaimer, the term of this patent is extended or adjusted under 35 U.S.C. 154(b) by 859 days.

This patent is subject to a terminal disclaimer.

(21) Appl. No.: 10/811,413

(22) Filed: Mar. 26, 2004

(65) Prior Publication Data

US 2005/0123582 A1    Jun. 9, 2005

Related U.S. Application Data

(63) Continuation-in-part of application No. 10/717,162, filed on Nov. 19, 2003, which is a continuation-in-part of application No. 10/610,391, filed on Jun. 30, 2003, now abandoned, which is a continuation-in-part of application No. 10/211,656, filed on Aug. 2, 2002, now Pat. No. 6,624,138, which is a continuation-in-part of application No. 09/297,808, filed as application No. PCT/US97/20113 on Nov. 4, 1997, now Pat. No. 6,608,040.

(60) Provisional application No. 60/552,517, filed on Mar. 12, 2004, provisional application No. 60/547,935, filed on Feb. 26, 2004, provisional application No. 60/518,050, filed on Nov. 7, 2003, provisional application No. 60/492,874, filed on Aug. 6, 2003, provisional application No. 60/030,701, filed on Nov. 5, 1996.

(51) Int. Cl.
*A61F 13/00* (2006.01)
(52) U.S. Cl. .................................... 424/422
(58) Field of Classification Search ............... 424/422; 623/1.16, 1.38, 1.42, 1.44–1.48
See application file for complete search history.

(56) References Cited

U.S. PATENT DOCUMENTS 4,806,595 A    2/1989   Noishiki et al.

(Continued)

OTHER PUBLICATIONS

Radar DS, "High-Density Lipoproteins as an Emerging Therapeutic Target for Atherosclerosis", JAMA 2003;290(17): 2322-2324.
Nissen SE et al., "Effect of Recombinant ApoA-I Milano on Coronary Atherosclerosis in Patients With Acute Coronary Symdroms", JAMA 2003; 290(17): 2292-2300.

(Continued)

*Primary Examiner*—Sharon E. Kennedy

(57) ABSTRACT

A method for treating vulnerable plaques of a patient, comprising: providing a biodegradable stent comprising a first supporting zone made of a first biodegradable material, wherein the supporting zone comprises at least a portion of continuous circumference of the stent; and a second therapeutic zone made of a second biodegradable material, wherein the therapeutic zone comprises at least one bioactive agent; delivering the biodegradable stent to the vulnerable plaques; orienting the therapeutic zone at about the luminal surface of the vulnerable plaque; and releasing the at least one bioactive agent for treating the vulnerable plaques.

12 Claims, 12 Drawing Sheets

U.S. PATENT DOCUMENTS

| | | | |
|---|---|---|---|
| 5,037,664 A | 8/1991 | Kyogoku et al. | |
| 5,085,629 A | 2/1992 | Goldberg et al. | |
| 5,270,446 A | 12/1993 | Kyogoku et al. | |
| 5,290,271 A * | 3/1994 | Jernberg | 604/891.1 |
| 5,322,935 A | 6/1994 | Smith | |
| 5,464,450 A | 11/1995 | Buscemi et al. | |
| 5,516,781 A | 5/1996 | Morris et al. | |
| 5,545,208 A * | 8/1996 | Wolff et al. | 623/1.22 |
| 5,693,085 A * | 12/1997 | Buirge et al. | 623/1.13 |
| 5,733,327 A | 3/1998 | Igaki et al. | |
| 5,780,052 A | 7/1998 | Khaw et al. | |
| 5,929,038 A | 7/1999 | Chang | |
| 6,045,568 A | 4/2000 | Igaki et al. | |
| 6,071,305 A * | 6/2000 | Brown et al. | 623/1.43 |
| 6,080,177 A | 6/2000 | Igaki et al. | |
| 6,103,255 A | 8/2000 | Levene et al. | |
| 6,120,535 A * | 9/2000 | McDonald et al. | 623/1.39 |
| 6,160,084 A | 12/2000 | Langer et al. | |
| 6,162,826 A | 12/2000 | Moon et al. | |
| 6,200,335 B1 | 3/2001 | Igaki | |
| 6,206,931 B1 | 3/2001 | Cook et al. | |
| 6,245,103 B1 * | 6/2001 | Stinson | 623/1.22 |
| 6,262,083 B1 | 7/2001 | Moon et al. | |
| 6,264,992 B1 | 7/2001 | Voytik-Harbin et al. | |
| 6,388,043 B1 | 5/2002 | Langer et al. | |
| 6,395,300 B1 | 5/2002 | Straub et al. | |
| 6,423,682 B1 | 7/2002 | Ballinger et al. | |
| 6,436,703 B1 | 8/2002 | Tang et al. | |
| 6,451,764 B1 | 9/2002 | Lee et al. | |
| 6,475,784 B1 | 11/2002 | Papkoff | |
| 6,476,211 B1 | 11/2002 | Ford et al. | |
| 6,485,920 B1 | 11/2002 | Ballinger et al. | |
| 6,544,544 B2 | 4/2003 | Hunter et al. | |
| 6,608,040 B1 | 8/2003 | Lin et al. | |
| 6,624,138 B1 * | 9/2003 | Sung et al. | 514/1 |
| 6,632,242 B2 | 10/2003 | Igaki | |
| 6,699,280 B2 * | 3/2004 | Camrud et al. | 623/1.16 |
| 6,806,257 B1 * | 10/2004 | Lee et al. | 514/23 |
| 6,827,737 B2 * | 12/2004 | Hill et al. | 623/1.4 |
| 2001/0034550 A1 * | 10/2001 | Buirge et al. | 623/1.47 |
| 2002/0058986 A1 * | 5/2002 | Landau et al. | 623/1.13 |
| 2002/0082680 A1 * | 6/2002 | Shanley et al. | 623/1.16 |
| 2002/0133223 A1 * | 9/2002 | Vito et al. | 623/1.18 |
| 2003/0004568 A1 * | 1/2003 | Ken et al. | 623/1.46 |
| 2003/0055198 A1 | 3/2003 | Langer et al. | |
| 2003/0109442 A1 * | 6/2003 | Bisgaier et al. | 514/12 |
| 2003/0135265 A1 * | 7/2003 | Stinson | 623/1.16 |
| 2003/0153972 A1 * | 8/2003 | Helmus | 623/1.15 |
| 2004/0015187 A1 | 1/2004 | Lendlein et al. | |
| 2004/0024448 A1 * | 2/2004 | Chang et al. | 623/1.42 |
| 2004/0034409 A1 * | 2/2004 | Heublein et al. | 623/1.46 |
| 2004/0039441 A1 * | 2/2004 | Rowland et al. | 623/1.42 |
| 2004/0142014 A1 * | 7/2004 | Litvack et al. | 424/423 |
| 2004/0142902 A1 * | 7/2004 | Struijker-Boudier | 514/53 |
| 2004/0202692 A1 * | 10/2004 | Shanley et al. | 424/426 |
| 2004/0215338 A1 * | 10/2004 | Elkins et al. | 623/1.46 |
| 2004/0220660 A1 * | 11/2004 | Shanley et al. | 623/1.16 |
| 2004/0220665 A1 * | 11/2004 | Hossainy et al. | 623/1.42 |
| 2005/0119723 A1 * | 6/2005 | Peacock, III | 623/1.15 |
| 2005/0163818 A1 * | 7/2005 | Sung et al. | 424/423 |
| 2005/0233992 A1 * | 10/2005 | Itescu | 514/44 |
| 2006/0034885 A1 * | 2/2006 | Sung et al. | 424/422 |
| 2006/0095058 A1 * | 5/2006 | Sivan et al. | 606/170 |
| 2006/0287710 A1 * | 12/2006 | Lendlein et al. | 623/1.19 |
| 2007/0078513 A1 * | 4/2007 | Campbell | 623/1.44 |
| 2007/0141100 A1 * | 6/2007 | Sung et al. | 424/423 |

OTHER PUBLICATIONS

Naghavi M et al., "From Vulnerable Plaque to Vulnerable Patient-Part I" Circulation 2003; 108: 1664-1672.

Naghavi M et al., "From Vulnerable Plaque to Vulnerable Patient—Part II" Circulation 2003; 108: 1772-1778.

Sung HW et al., "Feasibility Study of a Natural Crosslinking Reagent for Biological Tissue Fixation" J Biomed Mater Res 1998; 42: 560-567.

Huang LL et al., "Biocompatibility Study of a Biological Tissue Fixed With a Naturally Occurring Crosslinking Reagent" J Biomed Mater Res 1998; 42: 568-576.

Sung HW et al., "In Vitro Evaluation of Cytotoxicity of a Naturally Occurring Cross-Linking Reagent for Biological Tissue Fixation", J Biomater Sci Polymer Edn 1999; 10(1): 63-78.

Sung HW et al., "A Naturally Occurring Reagent for Biological Tissue Fixation" in New Biomedical Materials, Edited by Haris PI and Chapman D, pp. 182-191 (1998), Published by IOS Press.

Sung HW et al., "Crosslinking Characteristics and Mechanical Properties of a Bovine Pericardium Fixed With a Naturally Occurring Crosslinking Agent" J Biomed Mater Res 1999; 47: 116-126.

Sung HW et al., "Mechanical Properties of a Porcine Aortic Valve Fixed With a Naturally Occurring Crosslinking Agent" Biomaterials 1999; 20: 1759-1772.

Sung HW et al., "In Vitro Surface Characterization of a Biological Patch Fixed With a Naturally Occurring Crosslinking Agent" Biomaterials 2000; 21: 1353-1362.

Tsai CC et al., "In Vitro Evaluation of the Genotoxicity of a Naturally Occurring Crosslinking Agent (Genipin) for Biologic Tissue Fixation" J Biomed Mater Res 2000; 52: 58-65.

Sung HW et al., "Fixation of Biological Tissues With a Naturally Occurring Crosslinking Agent: Fixation Rate and Effects of PH, Temperature, and Initial Fixative Concentration" J Biomed Mater Res 2000; 52: 77-87.

Sung HW et al., "Extraction of a Naturally Occurring Crosslinking Agent (Genipin) From Gardenia Fruits and its Applications in Biological Tissue Fixation" in Biomaterials and Drug Delivery Toward New Millenium, Edited by Park KD et al., pp. 623-632 (2000), Published by Han Rin Won Publishing Co.

Tsai CC et al., "Effects of Heparin Immobilization on the Surface Characteristics of a Biological Tissue Fixed With a Naturally Occurring Crosslinking Agent" Biomaterials 2001; 22: 523-533.

Sung HW et al., "Stability of a Biological Tissue Fixed With a Naturally Occurring Croslinking Agent (Genipin)" J Biomed Mater Res 2001; 55: 538-546.

Chang Y et al., "Reconstruction of the Right Ventricular Outflow Tract With a Bovine Jugular Vein Graft Fixed With a Naturally Occurring Crosslinking Agent (Genipin) in a Canine Model" J Thorac Cardiovasc Surg 2001; 122: 1208-1218.

Mi FL et al., "In Vivo Biocompatibility and Degradability of a Novel Injectable-Chitosan-Based Implant" Biomaterials 2002; 23: 181-191.

Mi FL et al., "Drug Release From Chitosan-Alginate Complex Beads Reinforced by a Naturally Occurring Cross-Linking Agent" Carbohydrate Polymers 2002; 48: 61-72.

Chang Y et al., "In Vivo Evaluation of Cellular and Acellular Bovine Pericardia Fixed With a Naturally Occurring Crosslinking Agent (Genipin)" Biomaterials 2002; 23: 2447-2457.

Liang HC et al., "Genipin-Crosslinked Gelatin Microspheres as a Drug Carrier for Intramuscular Administration-In Vitro and In Vivo Studies" J Biomed Mater Res 2003; 65A: 271-282.

Biocompatibles "PC Technology Overview" 2004.

News Release "TCT: ABT-578-Eluting Stent Demonstrates Robust Results" Washington DC, Sep. 23, 2003.

News Release "First Human Implant Heralds Next Generation of Coronary Stent System" Santa Rose, CA, Jan. 7, 2003.

News Release "Endeavor I: IVUS Analysis of ABT-578-Eluting Stent Trial Confirms Early Safety" New Orleans, LA, ACC2004.

* cited by examiner

Genipin
(GP)

Glutaraldehyde
(GA)

DRUG-ELUTING STENT HAVING COLLAGEN DRUG CARRIER CHEMICALLY TREATED WITH GENIPIN

CROSS-REFERENCE TO RELATED APPLICATIONS

This application is a continuation-in-part application of U.S. patent application Ser. No. 10/717,162 filed Nov. 19, 2003, entitled "Crosslinkable Collagen as Medical Material", which is a continuation-in-part application of application Ser. No. 10/610,391 filed Jun. 30, 2003, now abandoned entitled "Drug-eluting Device Chemically Treated with Genipin", which is a continuation-in-part application of application Ser. No. 10/211,656 filed Aug. 2, 2002, entitled "Drug-loaded Biological Material Chemically Treated with Genipin", now U.S. Pat. No. 6,624,138, which is a continuation-in-part application of application Ser. No. 09/297,808 filed Sep. 27, 2001, now U.S. Pat. No. 6,608,040, which is the national stage entry of PCT/US97/20113 filed Nov. 4, 1997, which claims the benefits of a provisional application Ser. No. 60/030,701 filed Nov. 5, 1996. The application also claims the benefits of provisional application Ser. No. 60/492,874 filed Aug. 6, 2003, application Ser. No. 60/518,050 filed Nov. 7, 2003, application Ser. No. 60/547,935 filed Feb. 26, 2004, and application Ser. No. 60/552,517 filed Mar. 12, 2004. Entire contents of all the above co-pending applications are incorporated herein by reference.

FIELD OF THE INVENTION

The prestent invention generally relates to chemical modification of biomedical materials, such as collagen matrix with a naturally occurring crosslinking reagent, genipin. More particularly, the prestent invention relates to crosslinkable collagen as medical material or further loaded with a plurality of bioactive agents that is configured suitable for general drug slow release effective for therapeutic purposes by each of the plural drugs, wherein the medical material is crosslinkable with a crosslinking reagent, genipin, its derivatives or analog, or crosslinked with ultraviolet. Further, the prestent invention relates to a biodegradable stent for treating vulnerable plaques of a patient comprising at least two zones, wherein a first supporting zone comprises at least a portion of continuous circumference of the stent, the supporting zone being made of a first biodegradable material; and a second therapeutic zone made of a second biodegradable material.

BACKGROUND OF THE INVENTION

Crosslinking of Biological Material

Crosslinking of biological molecules is often desired for optimum effectiveness in biomedical applications. For example, collagen, which constitutes the structural framework of biological tissue, has been extensively used for manufacturing bioprostheses and other implanted structures, such as vascular grafts, wherein it provides a good medium for cell infiltration and proliferation. However, biomaterials derived from collagenous tissue must be chemically modified and subsequently sterilized before they can be implanted in humans. The fixation, or crosslinking, of collagenous tissue increases strength and reduces antigenicity and immunogenicity. In one aspect of the prestent invention, crosslinking of a drug-containing biological material with genipin enables the resulting material ("biological substance") with less antigenicity or immunogenicity, wherein the biological material comprises collagen, gelatin, elastin, chitosan, N, O, carboxylmethyl chitosan (NOCC), and the like that has at least one amino functional group for reaction with genipin.

Collagen sheets are also used as wound dressings, providing the advantages of high permeability to water vapor and rapid wound healing. Disadvantages include low tensile strength and easy degradation of collagen by collagenase. Crosslinking of collagen sheets reduces cleavage by collagenase and improves tensile strength. In one aspect of the prestent invention, a collagen strip derived of crosslinked drug-containing collagen sheets may be used to load on the periphery of a stent as a drug-eluting stent to mitigate restenosis or other abnormality. In a further aspect of the prestent invention, the collagen sheet or collagen strip may be made of solidifiable collagen.

Clinically, biological tissue has been used in manufacturing heart valve prostheses, small-diameter vascular grafts, ligament replacements, and biological patches, among others. However, the biological tissue has to be fixed with a crosslinking or chemically modifying agent and subsequently sterilized before they can be implanted in humans. The fixation of biological tissue or collagen is to reduce antigenicity and immunogenicity and prevent enzymatic degradation. Various crosslinking agents have been used in fixing biological tissue. These crosslinking agents are mostly synthetic chemicals such as formaldehyde, glutaraldehyde, dialdehyde starch, glyceraldehydes, cyanamide, diimides, diisocyanates, dimethyl adipimidate, carbodiimide, and epoxy compound. However, these chemicals are all highly cytotoxic which may impair the biocompatibility of biological tissue. Of these, glutaraldehyde is known to have allergenic properties, causing occupational dermatitis and is cytotoxic at concentrations greater than 10-25 ppm and as low as 3 ppm in tissue culture. It is therefore desirable to provide a crosslinking agent (synonymous to a crosslinking reagent) suitable for use in biomedical applications that is within acceptable cytotoxicity and that forms stable and biocompatible crosslinked products.

An example of a genipin-crosslinked heart valve is reported by Sung et al., a co-inventor of the prestent invention, (Journal of Thoracic and Cardiovascular Surgery vol. 122, pp. 1208-1218, 2001) entitled *Reconstruction of the right ventricular outflow tract with a bovine jugular vein graft fixed with a naturally occurring crosslinking agent (genipin) in a canine model*, entire contents of which are incorporated herein by reference. Sung et al. herein discloses genipin and its crosslinking ability to a collagen-containing biological tissue heart valve used in an animal implantation study.

To achieve this goal, a naturally occurring crosslinking agent (genipin) has been used to fix biological tissue. The co-pending application Ser. No. 09/297,808 filed Nov. 4, 1997, entitled "Chemical modification of biomedical materials with genipin" and its PCT counterpart, WO 98/19718, are incorporated and cited herein by reference. The cytotoxicity of genipin was previously studied in vitro using 3T3 fibroblasts, indicating that genipin is substantially less cytotoxic than glutaraldehyde (Sung H W et al., J Biomater Sci Polymer Edn 1999; 10:63-78). Additionally, the genotoxicity of genipin was tested in vitro using Chinese hamster ovary (CHO-K1) cells, suggesting that genipin does not cause clastogenic response in CHO-K1 cells (Tsai C C et al., J Biomed Mater Res 2000; 52:58-65), incorporated herein by reference. A biological material (including collagen-containing or chitosan-containing substrate) treated with genipin resulting in acceptable cytotoxicity is a first requirement to biomedical applications.

In a co-pending application by one inventor of the prestent application, U.S. patent application Ser. No. 10/067,130 filed Feb. 4, 2002 entitled Acellular Biological Material Chemically Treated with Genipin, entire contents of which are incorporated herein by reference, discloses an acellular tissue providing a natural microenvironment for host cell migration, in vitro endothelialization, or in vivo endothelialization to accelerate tissue regeneration. The genipin-treated biological biomaterial has reduced antigenicity and immunogenicity.

Restenosis in Angioplasty and Stenting

Atherosclerosis causes a partial blockage of the blood vessels that supply the heart with nutrients. Atherosclerotic blockage of blood vessels often leads to hypertension, ischemic injury, stroke, or myocardial infarction. Typically angioplasty and/or stenting is a remedy for such a disease, however, restenosis does occur in 30-40 percent patients resulting from intimal smooth muscle cell hyperplasia. The underlying cause of the intimal smooth muscle cell hyperplasia is mainly vascular smooth muscle injury and disruption of the endothelial lining.

Vascular injury causing intimal thickening can be from mechanical injuries due to angioplasty and/or stenting. Intimal thickening following balloon catheter injury has been studied in animals as a model for arterial restenosis that occurs in human patients following balloon angioplasty. Injury is followed by a proliferation of the medial smooth muscle cells, after which many of them migrate into the intima through fenestrate in the internal elastic lamina and proliferate to form a neointimal lesion.

Vascular stenosis can be detected and evaluated using angiographic or sonographic imaging techniques and is often treated by percutaneous transluminal coronary angioplasty (balloon catheterization). Within a few months following angioplasty, however, the blood flow is reduced in approximately 30-40 percent of these patients as a result of restenosis caused by a response to mechanical vascular injury suffered during the angioplasty or stenting procedure, as described above.

In an attempt to prevent restenosis or reduce intimal smooth muscle cell proliferation following angioplasty, numerous pharmaceutical agents have been employed clinically, concurrent with or following angioplasty. Most pharmaceutical agents employed in an attempt to prevent or reduce the extent of restenosis have been unsuccessful. The following list identifies several of the agents for which favorable clinical results have been reported: lovastatin; thromboxane $A_2$ synthetase inhibitors such as DP-1904; eicosapentanoic acid; ciprostene (a prostacyclin analog); trapidil (a platelet derived growth factor)]; angiotensin convening enzyme inhibitors; and low molecular weight heparin, entire contents of the above-referred drugs and their therapeutic effects are incorporated herein by reference. It is one aspect of the prestent invention to provide site-specific administration of the pharmaceutical agents disclosed in this invention to the injury site for effective therapy via a genipin-crosslinked collagen-containing or chitosan-containing biological carrier.

Many compounds have been evaluated in a standard animal model. The immunosuppressive agent cyclosporin A has been evaluated and has produced conflicting results. Jonasson reported that cyclosporin A caused an inhibition of the intimal proliferative lesion following arterial balloon catheterization in vivo, but did not inhibit smooth muscle cell proliferation in vitro. It was reported that when de-endothelialized rabbits were treated with cyclosporin A, no significant reduction of intimal proliferation was observed in vivo. Additionally, intimal accumulations of foamy macrophages, together with a number of vacuolated smooth muscle cells in the region adjacent to the internal elastic lamina were observed, indicating that cyclosporin A may modify and enhance lesions that form at the sites of arterial injury.

Morris et al. in U.S. Pat. No. 5,516,781 disclosed Rapamycin (also known as sirolimus), a macrocyclic triene antibiotic produced by *Streptomyces hygroscopicus* that has been shown to prevent the formation of humoral (IgE-like) antibodies in response to an albumin allergic challenge, inhibit murine T-cell activation, prolong survival time of organ gratis in histoincompatible rodents, and inhibit transplantation rejection in mammals. Rapamycin blocks calcium-dependent, calcium-independent, cytokine-independent and constitutive T and B cell division at the G1-S interface. Rapamycin inhibits gamma-interferon production induced by Il-1 and also inhibits the gamma-interferon induced expression of membrane antigen. Arterial thickening following transplantation, known as CGA, is a limiting factor in graft survival that is caused by a chronic immunological response to the transplanted blood vessels by the transplant recipient's immune system.

Further, Morris et al. in U.S. Pat. No. 5,516,781 claims the invention is distinct from the use of rapamycin for preventing CGA, in that CGA does not involve injury to the recipients' own blood vessels; it is a rejection type response. The disclosed patent '781 is related to vascular injury to native blood vessels. The resulting intimal smooth muscle cell proliferation does not involve the immune system, but is growth factor mediated. For example, arterial intimal thickening after balloon catheter injury is believed to be caused by growth factor (PGDF, bFGF, TGFb, IL-1 and others)-induced smooth muscle cell proliferation and migration. The above-cited U.S. Pat. No. 5,516,781 is incorporated herein by reference.

In the past, polymer or plastic materials have been used as a carrier for depositing a drug or pharmaceutical agent onto the periphery of a stent to treat restenosis. Example is U.S. Pat. No. 6,544,544 to Hunter et al., entire contents of which are incorporated herein by reference. Hunter et al. discloses a method for treating a tumor excision site, comprising administering to a patient a composition comprising paclitaxel, or an analogue or derivative thereof, to the resection margin of a tumor subsequent to excision, such that the local recurrence of cancer and the formation of new blood vessels at the site is inhibited. The composition further comprises a polymer, wherein the polymer may comprise poly(caprolactone), poly(lactic acid), poly(ethylene-vinyl acetate), and poly(lactic-co-glycolic)acid.

In another example, Biocompatibles PC (phosphorylcholine by Biocompatibles, London, England) has been added as a drug carrier or surface modifier for treating tissue injury due to angioplasty and/or stenting. The technique comprises a hydrophobic component that aids in the initial adhesion and film-formation of the polymer onto the stainless steel stent substrate, and other groups allow cross-linking both within the polymer and with the stent surface to achieve firm anchorage. The coating is thus tenaciously adhered to the stent and can survive balloon expansion without damage. A therapeutic drug can be loaded within the coated substrate, such as phosphorylcholine.

Drugs are usually loaded, admixed or entrapped physically within the polymer framework for slow drug release. The plastic polymer which is suitable as a drug carrier may not be biocompatible, whereas some biocompatible plastic polymer may not be able to contain a specific drug and release drug in an effective timely amount for effective therapy. Therefore, there is a clinical need to have a biocompatible drug carrier that releases an effective quantity of drug over a period of time for prolonged therapeutic effects.

U.S. Pat. No. 5,085,629 issued on Feb. 4, 1992, entire contents of which are incorporated herein by reference, discloses a biodegradable, biocompatible, resorbable infusion stent comprising a terpolymer of: (a) L(−)lactide, (b) glycolide, and (c) epsilon-caprolactone. This invention includes a method for treating ureter obstructions or impairments by utilizing a biodegradable, biocompatible, resorbable infusion stent, and a method for controlling the speed of resorption of the stent. A ureter stent that is made of a biodegradable and biocompatible material would assure its safe and innocuous disappearance without the need for a second surgical procedure for its removal after it has completed its function.

U.S. Pat. No. 5,464,450 issued on Nov. 7, 1995, entire contents of which are incorporated herein by reference, discloses a stent made of biodegradable material including a drug that is released at a rate controlled by the rate of degradation of the biodegradable material. The stent includes a main body of a generally tubular shape. The main body may further include a plurality of apertures extending therethrough and a slot defined by opposing edges which permits insertion and positioning of the stent.

U.S. Pat. No. 6,200,335 issued on Mar. 13, 2001 and No. 6,632,242 issued on Oct. 14, 2003, entire contents of which are incorporated herein by reference, discloses a stent for a vessel inserted in use into the vessel of a living body including a tubular member constituting a passageway from one end to its opposite end. The tubular member includes a main mid portion and low tenacity portions formed integrally with both ends of the main mid portion. The low tenacity portions are lower in tenacity than the main mid portion. These low tenacity portions are formed so as to have the Young's modulus approximate to that of the vessel of the living body in which is inserted the stent, so that, when the stent is inserted into the vessel, it is possible to prevent stress concentrated portions from being produced in the vessel.

In accordance with the prestent invention there is provided genipin treated collagen-containing or chitosan-containing biological material loaded with at least one drug for implant and other surgical applications which have shown to exhibit many of the desired characteristics important for optimal therapeutic function. In particular, the crosslinked collagen-drug compound with drug slow release capability may be suitable as anti restenosis agent in treating atherosclerosis and other therapeutic applications.

SUMMARY OF THE INVENTION

In general, it is an object of the prestent invention to provide a biological substance configured and adapted for drug slow release. In one aspect of the prestent invention, the biological substance may be adhesively loaded onto a stent surface rendering the stent to slowly release drug from the biological substance. The "biological substance" is herein intended to mean a substance made of drug-containing biological material that is, in one preferred embodiment, solidifiable upon change of environmental condition(s) and is biocompatible post-crosslinking with a crosslinker, such as genipin, its derivatives, analog, stereoisomers and mixtures thereof. In one embodiment, the crosslinker may further comprise epoxy compounds, dialdehyde starch, glutaraldehyde, formaldehyde, dimethyl suberimidate, carbodiimides, succinimidyls, diisocyanates, acyl azide, ultraviolet irradiation, dehydrothermal treatment, tris(hydroxymethyl) phosphine, ascorbate-copper, glucose-lysine and photo-oxidizers, and the like. The "biological material" is intended herein to mean collagen, gelatin, elastin, chitosan, NOCC (N, O, carboxylmethyl chitosan), and the like that could be crosslinked with a crosslinker (also known as a crosslinking agent).

In one embodiment, the process of preparing a biological substance comprises steps, in combination, of loading drugs with the biological material, shaping the drug-containing biological material, followed by crosslinking with genipin. The genipin referred herein is broadly consisted of the naturally occurring compound as shown in FIG. 1 and its derivatives, analog, stereoisomers and mixtures thereof. In another embodiment, the drug-containing biological material is further coated, adhered or loaded onto a physical construct or apparatus before or after crosslinking with a crosslinker (such as genipin). The biological material is herein broadly generally referred to collagen, elastin, gelatin, chitosan, NOCC, the mixtures thereof, and derivates, analog and mixtures thereof. The biological material may be in a form or phase of solution, paste, gel, suspension, colloid or plasma that is solidifiable thereafter.

It is another object of the prestent invention to provide a method for drug slow release from a medical device comprising entrapping drug within a biological material crosslinked with genipin. The medical device can be a stent (biodegradable or non biodegradable), a non-stent implant or prosthesis, or a percutaneous device such as a catheter, a wire, a cannula, an endoscopic instrument or the like for the intended drug slow release. In one embodiment, the non-stent implant may comprise biological implant, non-biological implant, annuloplasty rings, heart valve prostheses, venous valve bioprostheses, orthopedic implants, dental implants, ophthalmology implants, cardiovascular implants, and cerebral implants.

It is a further object of the prestent invention to provide a method for drug slow release from an implant comprising chemically bonding ionically or covalently drug within a biological material crosslinked with genipin, wherein the drug has an amine or amino group branch. In one aspect of the prestent invention, the amine or amino group of the drug is reacted with the amino group of collagen through a crosslinker.

Some aspects of the invention relate to a vascular stent, comprising a biodegradable or non biodegradable stent base coated with at least one layer of partially crosslinked collagen. In one embodiment, the at least one collagen layer comprises a drug or drugs, each collagen layer comprising different drug content, drug type, drug concentration, or combination thereof. Some preferred aspect of the invention provides a medical device comprising a biodegradable apparatus having a surface, at least one bioactive agent, and biological material loaded onto at least a portion of the surface of the apparatus, the biological material comprising the at least one bioactive agent, wherein the biological material is crosslinked with a crosslinking agent or with ultraviolet irradiation.

Some aspects of the invention relate to a method for treating a target tissue of a patient comprising providing a medical device that comprises a biodegradable apparatus having a surface, wherein a biological material loaded onto at least a portion of the surface of the apparatus, the biological material comprising at least one bioactive agent; crosslinking the biological material with a crosslinking agent or with ultraviolet irradiation; and delivering the medical device to the target tissue and releasing the bioactive agent for treating the target tissue.

Some aspects of the invention relate to a biodegradable stent for treating vulnerable plaques of a patient comprising at least two zones, wherein a first supporting zone comprises at least a portion of continuous circumference of the stent, said supporting zone being made of a first biodegradable material; and a second therapeutic zone made of a second biodegradable material.

Some aspects of the invention relates to the biodegradable stent of the invention, wherein the biodegradation rate of said second biodegradable material is equal to or faster than the biodegradation rate of said first biodegradable material.

Some aspects of the invention relates to the biodegradable stent of the invention, wherein at least one of the first and the second biodegradable material is a shape memory polymer.

Some aspects of the invention relates to the biodegradable stent of the invention, wherein at least one of the first and the second biodegradable material further comprises a biological material, wherein said biological material is phosphorylcholine.

Some aspects of the invention relates to the biodegradable stent of the invention, wherein at least one of the first and the second biodegradable material further comprises a biological material, wherein said biological material is crosslinked with a crosslinking agent or with ultraviolet irradiation.

Some aspects of the invention relates to the biodegradable stent of the invention, wherein at least one of the first and the second biodegradable material further comprises a biological material, wherein said biological material is crosslinked with a crosslinking agent, wherein the crosslinking agent is genipin, its analog, derivatives, and combination thereof.

Some aspects of the invention relates to the biodegradable stent of the invention, wherein the biodegradable material in the therapeutic zone or the supporting zone further comprises a biological material, wherein said biological material is crosslinked with a crosslinking agent, wherein the crosslinking agent is selected from a group consisting of formaldehyde, glutaraldehyde, dialdehyde starch, glyceraldehydes, cyanamide, diimides, diisocyanates, dimethyl adipimidate, carbodiimide, epoxy compound, and mixture thereof.

Some aspects of the invention relates to the biodegradable stent of the invention, wherein the biodegradable material in the therapeutic zone or the supporting zone further comprises a biological material, wherein the biological material is selected from a group consisting of collagen, gelatin, elastin, chitosan, N, O, carboxylmethyl chitosan, and mixture thereof.

Some aspects of the invention relates to the biodegradable stent of the invention, wherein the biodegradable material in the therapeutic zone or the supporting zone further comprises a biological material, wherein the biological material is a solidifiable substrate, and wherein the biological material is solidifiable from a phase selected from a group consisting of solution, paste, gel, suspension, colloid, and plasma.

Some aspects of the invention relates to the biodegradable stent of the invention, wherein the biodegradable material in the therapeutic zone or the supporting zone is made of a material selected from a group consisting of polylactic acid (PLA), polyglycolic acid (PGA), poly(D,L-lactide-co-glycolide), polycaprolactone, and co-polymers thereof.

Some aspects of the invention relates to the biodegradable stent of the invention, wherein the biodegradable material in the therapeutic zone or the supporting zone is made of a material selected from a group consisting of polyhydroxy acids, polyalkanoates, polyanhydrides, polyphosphazenes, polyetheresters, polyesteramides, polyesters, and polyorthoesters.

Some aspects of the invention relates to the biodegradable stent of the invention, wherein at least one of the first and the second biodegradable material comprises at least one bioactive agent.

Some aspects of the invention relates to the biodegradable stent of the invention, wherein at least one of the first and the second biodegradable material comprises a plurality of bioactive agents. In one embodiment, the bioactive agents are in the luminal surface and/or exterior surface.

Some aspects of the invention relates to the biodegradable stent of the invention, wherein at least one of the first and the second biodegradable material comprises a plurality of bioactive agents in distinct multi-layers.

Some aspects of the invention relates to the biodegradable stent of the invention, wherein phosphorylcholine is coated at the outermost layer of the stent.

Some aspects of the invention relates to the biodegradable stent of the invention, wherein at least one of the first and the second biodegradable material comprises at least one bioactive agent, wherein the at least one bioactive agent is selected from a group consisting of analgesics/antipyretics, antiasthamatics, antibiotics, antidepressants, antidiabetics, antifungal agents, antihypertensive agents, anti-inflammatories, antineoplastics, antianxiety agents, immunosuppressive agents, antimigraine agents, sedatives/hypnotics, antipsychotic agents, antimanic agents, antiarrhythmics, antiarthritic agents, antigout agents, anticoagulants, thrombolytic agents, antifibrinolytic agents, antiplatelet agents and antibacterial agents, antiviral agents, antimicrobials, and anti-infectives.

Some aspects of the invention relates to the biodegradable stent of the invention, wherein at least one of the first and the second biodegradable material comprises at least one bioactive agent, wherein the at least one bioactive agent is selected from a group consisting of actinomycin D, paclitaxel, vincristin, methotrexate, and angiopeptin, batimastat, halofuginone, sirolimus, tacrolimus, everolimus, ABT-578, tranilast, dexamethasone, and mycophenylic acid.

Some aspects of the invention relates to the biodegradable stent of the invention, wherein at least one of the first and the second biodegradable material comprises at least one bioactive agent, wherein the at least one bioactive agent is selected from a group consisting of lovastatin, thromboxane $A_2$ synthetase inhibitors, eicosapentanoic acid, ciprostene, trapidil, angiotensin convening enzyme inhibitors, aspirin, and heparin.

Some aspects of the invention relates to the biodegradable stent of the invention, wherein at least one of the first and the second biodegradable material comprises at least one bioactive agent, wherein the at least one bioactive agent is selected from a group consisting of allicin, ginseng extract, ginsenoside Rg1, flavone, *ginkgo biloba* extract, glycyrrhetinic acid, and proanthocyanides.

Some aspects of the invention relates to the biodegradable stent of the invention, wherein at least one of the first and the second biodegradable material comprises at least one bioactive agent, wherein the at least one bioactive agent comprises ApoA-I Milano or recombinant ApoA-I Milano/phospholipid complexes.

Some aspects of the invention relates to the biodegradable stent of the invention, wherein at least one of the first and the second biodegradable material comprises at least one bioactive agent, wherein the at least one bioactive agent comprises biological cells or endothelial progenitor cells.

Some aspects of the invention relates to the biodegradable stent of the invention, wherein at least one of the first and the second biodegradable material comprises at least one bioactive agent, wherein the at least one bioactive agent comprises lipostabil.

Some aspects of the invention relates to the biodegradable stent of the invention, wherein at least one of the first and the second biodegradable material comprises at least one bioactive agent, wherein the at least one bioactive agent comprises a growth factor, wherein the growth factor is selected from a group consisting of vascular endothelial growth factor, transforming growth factor-beta, insulin-like growth factor, platelet derived growth factor, fibroblast growth factor, and combination thereof.

Some aspects of the invention relates to the method for treating vulnerable plaques of a patient, comprising: providing a biodegradable stent comprising a first supporting zone made of a first biodegradable material, wherein said supporting zone comprises at least a portion of continuous circumference of the stent; and a second therapeutic zone made of a second biodegradable material, wherein the therapeutic zone comprises at least one bioactive agent; delivering said biodegradable stent to said vulnerable plaques; orienting the therapeutic zone at about the luminal surface of the vulnerable plaque; and releasing said at least one bioactive agent for treating the vulnerable plaques.

BRIEF DESCRIPTION OF THE DRAWINGS

Additional objects and features of the prestent invention will become more apparent and the invention itself will be best understood from the following Detailed Description of Exemplary Embodiments, when read with reference to the accompanying drawings.

DETAILED DESCRIPTION OF EXEMPLARY EMBODIMENTS

The following detailed description is of the best prestently contemplated modes of carrying out the invention. This description is not to be taken in a limiting sense, but is made merely for the purpose of illustrating general principles of embodiments of the invention.

Figure 1:
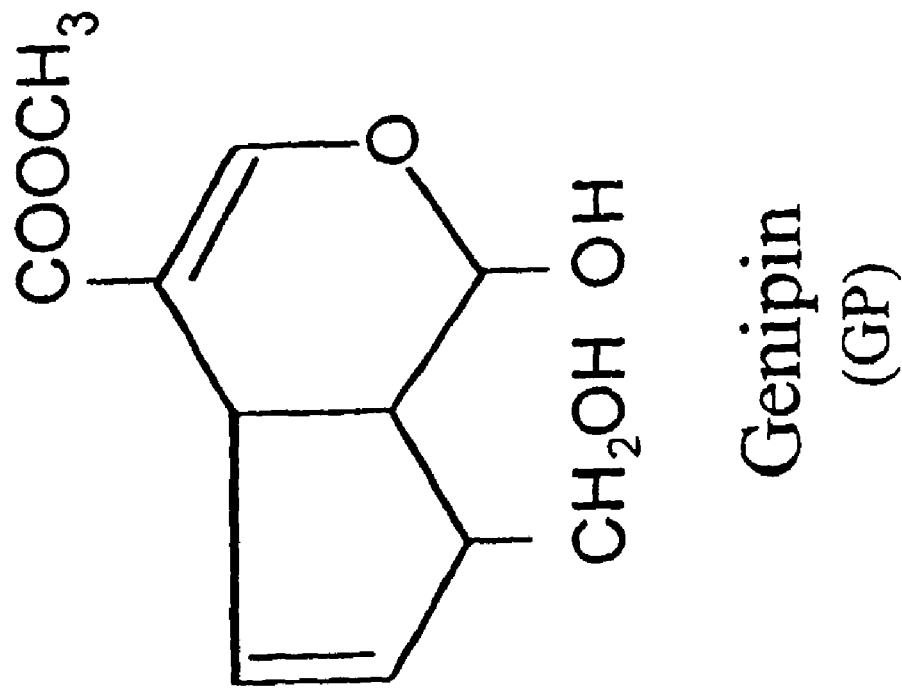
FIG. 1 is chemical structures of glutaraldehyde and genipin that are used in the chemical treatment examples of the current disclosure.
Figure 1:
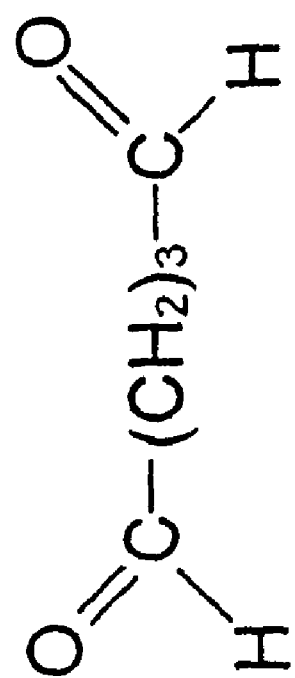

"Genipin" in this invention is meant to refer to the naturally occurring compound as shown in FIG. 1 and its derivatives, analog, stereoisomers and mixtures thereof.

"Crosslinking agent" is meant herein to indicate a chemical agent that could crosslink two molecules, such as formaldehyde, glutaraldehyde, dialdehyde starch, glyceraldehydes, cyanamide, diimides, diisocyanates, dimethyl adipimidate, carbodiimide, and epoxy compound.

"Biological material" is herein meant to refer to collagen extract, soluble collagen, elastin, gelatin, chitosan, chitosan-containing and other collagen-containing biological material. For a preferred aspect of the prestent invention, the biological material is meant to indicate a solidifiable biological substrate comprising at least a genipin-crosslinkable functional group, such as amino group or the like.

A "biological implant" refers to a medical device which is inserted into, or grafted onto, bodily tissue to remain for a period of time, such as an extended-release drug delivery device, drug-eluting stent, vascular or skin graft, or orthopedic prosthesis, such as bone, ligament, tendon, cartilage, and muscle.

In particular, the crosslinked collagen-drug device or compound with drug slow release capability may be suitable as anti restenosis agent in treating atherosclerosis and other therapeutic applications. In one aspect of the invention, it is provided a medical device comprising an apparatus (biodegradable or non biodegradable) having a surface (for example, a coronary stent), a bioactive agent, and biological material loaded onto at least a portion of the surface of the apparatus, the biological material comprising at least one bioactive agent, wherein the biological material is thereafter crosslinked with a crosslinking agent. In one preferred aspect, the device further comprises a biodegradable polymer loaded onto at least a portion of the surface of the apparatus, wherein the biodegradable polymer comprises at least one bioactive agent. In another aspect, the biological material comprises a solidifiable substrate and the device further comprises a step of solidifying the solidifiable substrate. In still another aspect, it is provided a medical device, comprising an apparatus having a surface (for example, a coronary stent or heart valve), at least one bioactive agent, and biological material, the biological material being crosslinked with a crosslinking agent, wherein the biological material is thereafter mixed with the bioactive agent and loaded onto at least a portion of the surface of the apparatus.

"Drug" in this invention is meant to broadly refer to a chemical molecule(s), biological molecule(s) or bioactive agent providing a therapeutic, diagnostic, or prophylactic effect in vivo. "Drug" and "bioactive agent" (interchangeable in meaning) may comprise, but not limited to, synthetic chemicals, biotechnology-derived molecules, herbs, cells, genes, growth factors, health food and/or alternate medicines. In the prestent invention, the terms "drug" and "bioactive agent" are used interchangeably.

A blood vessel is generally consisted of a support structure for transporting blood and a luminal blood-contacting surface lined with a layer of endothelial cells. On a denuded vessel surface, endothelialization, which involves the migration of endothelial cells from adjacent tissue onto the denuded luminal surface, can occur as a part of the healing process. Unfortunately, self-endothelialization occurs to only a limited degree and the limited endothelialization that does occur takes place slowly. To promote the rapid formation of an endothelial lining, endothelial cells can be seeded or loaded onto an implant, for example, a drug-eluting device of the prestent invention, before the implant is placed in the recipient. When the implant is placed in the recipient and exposed to physiologic blood flow, a portion of the endothelial cells at the device surface starts the process of endothelialization while another portion of the endothelial cells is slowly released to the device surface having delayed endothelialization.

The "biological substance" is herein intended to mean a substance made of drug-containing biological material that is, in one preferred embodiment, solidifiable upon change of environmental condition(s) and is biocompatible after being crosslinked with a crosslinker, such as genipin, epoxy compounds, dialdehyde starch, glutaraldehyde, formaldehyde, dimethyl adipimidate, carbodiimide, or the like.

The "biological material" is intended herein to mean collagen, gelatin, elastin, chitosan, N, O, carboxylmethyl chitosan (NOCC), chitosan-containing material, collagen-containing material, and the like that could be crosslinked, for example with a crosslinker (also known as a crosslinking agent) or with ultraviolet irradiation.

Preparation and Properties of Genipin

Figure 2A:
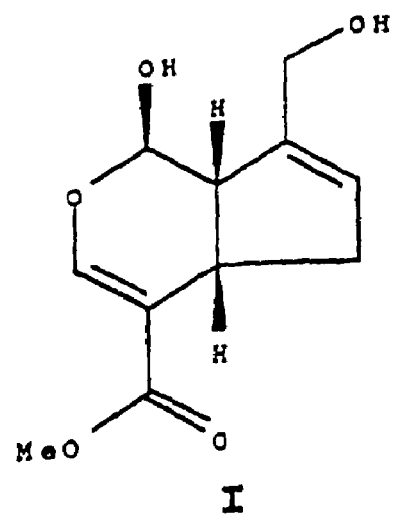
FIG. 2A is an iridoid glycoside prestent in fruits of *Gardenia jasmindides* Ellis (Structure I).
Figure 2B:
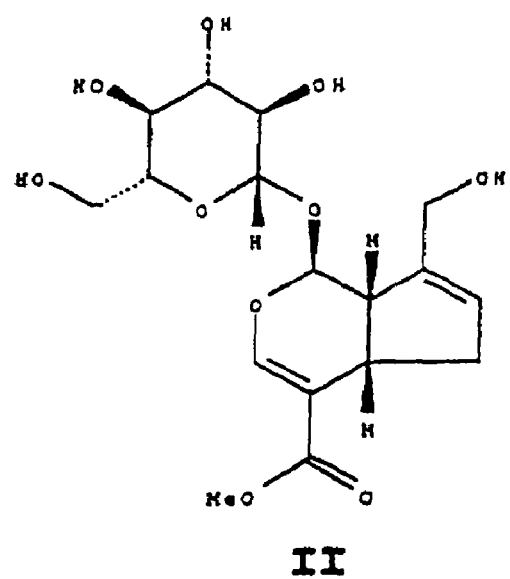
FIG. 2B is a parent compound geniposide (Structure II) from which genipin is derived.

Genipin, shown in Structure I of FIG. 2A, is an iridoid glycoside present in fruits (Gardenia jasmindides Ellis). It may be obtained from the parent compound geniposide, Structure II (FIG. 2B), which may be isolated from natural sources as described in elsewhere. Genipin, the aglycone of geniposide, may be prepared from the latter by oxidation followed by reduction and hydrolysis or by enzymatic hydrolysis. Alternatively, racemic genipin may be prepared synthetically. Although Structure I shows the natural configuration of genipin, any stereoisomer or mixture of stereoisomers of genipin as shown later may be used as a crosslinking reagent, in accordance with the prestent invention.

Genipin has a low acute toxicity, with $LD_{50}$ i.v. 382 mg/k in mice. It is therefore much less toxic than glutaraldehyde and many other commonly used synthetic crosslinking reagents. As described below, genipin is shown to be an effective crosslinking agent for treatment of biological materials intended for in vivo biomedical applications, such as prostheses and other implants, wound dressings, and substitutes.

It is one object of the prestent invention to provide a drug-collagen-genipin and/or drug-chitosan-genipin compound that is loaded onto the periphery of a cardiovascular stent enabling drug slow-release to the surrounding tissue, or to the lumen of the bodily cavity. In one preferred embodiment, the compound is loaded onto the outer periphery of the stent enabling drug slow-release to the surrounding tissue.

Previously, Chang in U.S. Pat. No. 5,929,038 discloses a method for treating hepatitis B viral infection with an iridoid compound of a general formula containing a six-member hydrocarbon ring sharing with one common bondage of a five-member hydrocarbon ring. Further, Moon et al. in U.S. Pat. Nos. 6,162,826 and 6,262,083 discloses genipin derivatives having anti hepatitis B virus activity and liver protection activity. All of which three aforementioned patents are incorporated herein by reference. The teachings of these patents do not disclose preparing tissue/device with scaffolds or collagen matrix with desirable porosity for use in tissue engineering, wherein the raw material source for tissue engineering is chemically modified by genipin, genipin derivatives or its analog with acceptably minimal cytotoxicity.

The genipin derivatives and/or genipin analog may have the following chemical formulas (Formula 1 to Formula 4):

(Genipin Analog Formula 1)

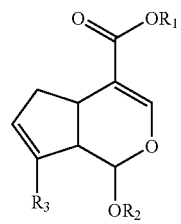

in which $R_1$ represents lower alkyl;

$R_2$ represents lower alkyl, pyridylcarbonyl, benzyl or benzoyl;

$R_3$ represents formyl, hydroxymethyl, azidomethyl, 1-hydroxyethyl, acetyl, methyl, hydroxy, pyridylcarbonyl, cyclopropyl, aminomethyl substituted or unsubstituted by (1,3-benzodioxolan-5-yl)carbonyl or 3,4,5-trimethoxybenzoyl, 1,3-benzodioxolan-5-yl, ureidomethyl substituted or unsubstituted by 3,4,5-trimethoxyphenyl or 2-chloro-6-methyl-3-pyridyl, thiomethyl substituted or unsubstituted by acetyl or 2-acetylamino2-ethoxycarbonyethyl, oxymethyl substituted or unsubstituted by benzoyl, pyridylcarbonyl or 3,4,5-trimethoxybenzoyl;

provided that $R_3$ is not methyl formyl, hydroxymethyl, acetyl, methylaminomethyl, acetylthiomethyl, benzoyloxymethyl or pyridylcarbonyloxymethyl when $R_1$ is methyl, and its pharmaceutically acceptable salts, or stereoisomers.

(Genipin Analog Formula 2)

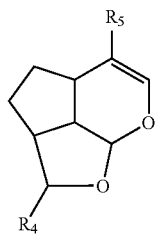

in which $R_4$ represtents lower alkoxy, benzyloxy, benzoyloxy, phenylthio, $C_1$~$C_{12}$ alkanyloxy substituted or unsubstituted by t-butyl, phenyl, phenoxy, pyridyl or thienyl;

$R_5$ represents methoxycarbonyl, formyl, hydroxyiminomethyl, methoxyimino-methyl, hydroxymethyl, phenylthiomethyl or acetylthiomethyl;

provided that $R_5$ is not methoxycarbonyl when $R_{14}$ is acetyloxy; and its pharmaceutically acceptable salts, or stereoisomers.

(Genipin Analog Formula 3)

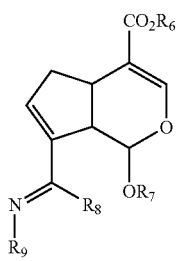

$R_6$ represents hydrogen atom, lower alkyl or alkalimetal;
$R_7$ represents lower alkyl or benzyl;
$R_8$ represents hydrogen atom or lower alkyl;
$R_9$ represents hydroxy, lower alkoxy, benzyloxy, nicotinoyloxy, isonicotinoyloxy, 2-pyridylmethoxy or hydroxycarbonylmethoxy;

provided that $R_9$ is not hydroxy or methoxy when $R_6$ is methyl and $R_8$ is hydrogen atom; and its pharmaceutically acceptable salts, or stereoisomers.

(Genipin Analog Formula 4)

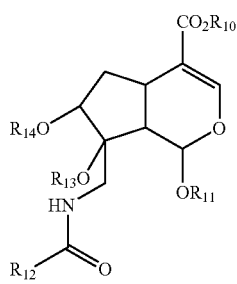

in which $R_{10}$ represents lower alkyl;
$R_{11}$ represents lower alkyl or benzyl;
$R_{12}$ represents lower alkyl, pyridyl substituted or unsubstituted by halogen, pyridylamino substituted or unsubstituted by lower alkyl or halogen, 1,3-benzodioxolanyl;
$R_{13}$ and $R_{14}$ each independently represent a hydrogen atom or join together to form isopropylidene; and
its pharmaceutically acceptable salts, or stereoisomers.

Kyogoku et al. in U.S. Pat. Nos. 5,037,664, 5,270,446, and EP 0366998, entire contents of all three being incorporated herein by reference, teach the crosslinking of amino group containing compounds with genipin and the crosslinking of genipin with chitosan. They also teach the crosslinking of iridoid compounds with proteins which can be vegetable, animal (collagen, gelatin) or microbial origin. However, they do not teach loading drug onto a collagen-containing biological material crosslinked with genipin as biocompatible drug carriers for drug slow-release.

Smith in U.S. Pat. No. 5,322,935, incorporated herein by reference in its entirety, teaches the crosslinking of chitosan polymers and then further crosslinking again with covalent crosslinking agents like glutaraldehyde. Smith, however, does not teach loading drug onto a chitosan-containing biological material crosslinked with genipin as biocompatible drug carriers for drug slow-release.

Noishiki et al. in U.S. Pat. No. 4,806,595 discloses a tissue treatment method by a crosslinking agent, polyepoxy compounds. Collagens used in that patent include an insoluble collagen, a soluble collagen, an atelocollagen prepared by removing telopeptides on the collagen molecule terminus using protease other than collagenase, a chemically modified collagen obtained by succinylation or esterification of above-described collagens, a collagen derivative such as gelatin, a polypeptide obtained by hydrolysis of collagen, and a natural collagen prestent in natural tissue (ureter, blood vessel, pericardium, heart valve, etc.) The Noishiki et al. patent is incorporated herein by reference. "Biological material" in the prestent invention is additionally used herein to refer to the above-mentioned collagen, collagen species, collagen in natural tissue, and collagen in a biological implant preform that are shapeable and/or solidifiable.

Voytik-Harbin et al. in U.S. Pat. No. 6,264,992 discloses submucosa as a growth substrate for cells. More particularly, the submucosa is enzymatically digested and gelled to form a shape retaining gel matrix suitable for inducing cell proliferation and growth both in vivo and in vitro. The Voytik-Harbin et al. patent is incorporated herein by reference. Biological material, additionally including submucosa, that is chemically modified or treated by genipin or other crosslinker of the prestent invention may serve as a shapeable raw material for making a biological substance adapted for inducing cell proliferation and ingrowth, but also resisting enzymatic degradation, both in vivo and in vitro. In a further aspect of the prestent invention, drug is loaded with submucosa biological material and crosslinked with a crosslinker, such as genipin.

Cook et al. in U.S. Pat. No. 6,206,931 discloses a graft prosthesis material including a purified, collagen-based matrix structure removed from a submucosa tissue source, wherein the submucosa tissue source is purified by disinfection and removal steps to deactivate and remove contaminants. The Cook et al. patent is incorporated herein by reference. Similarly, a collagen-based matrix structure, also known as "biological material" in this disclosure, may serve as a biomaterial adapted for medical device use after chemical modification by genipin of the present invention.

Levene et al. in U.S. Pat. No. 6,103,255 discloses a porous polymer scaffold for tissue engineering, whereby the scaffold is characterized by a substantially continuous solid phase, having a highly interconnected bimodal distribution of open pore sizes. The Levene et al. patent is incorporated herein by reference. The prestent invention discloses biological scaffold material by acellular process and acidic/enzymatic treatment adapted for tissue engineering. Additional benefits of genipin tissue treatment for reduced antigenicity, reduced cytotoxicity and enhanced biodurability on a drug-containing biological substance are disclosed in the prestent invention. Some aspects of the invention provide an acellular tissue with a natural or enlarged microenvironment for host cell migration, in vitro endothelialization, or in vivo endothelialization to accelerate tissue regeneration.

Several disadvantages are associated with the currently available technology. First, the prior art teaches collagen or chitosan in drug delivery application without suitable crosslinkage. The drug within collagen or chitosan matrix may tend to leach out in a short period of time because of no crosslinked barriers surrounding the drug. Another prior art teaches crosslinked collagen or chitosan without drug slow-release properties. It is esstential that drug is appropriately loaded within collagen or chitosan before the drug-containing collagen/chitosan is crosslinked enabling drug slow-release. Therefore, even if the two afore-mentioned prior arts were to be combined in a conventional manner, the combination would not show all of the novel physical feature and unexpected results of the present invention.

Collagen-Drug-Genipin Compound

In one embodiment of the present invention, it is disclosed that a method for treating tissue of a patient comprising, in combination, loading a drug-containing biological material onto an apparatus or medical device, an optional step of solidifying the drug-containing biological material, chemically treating the drug-containing biological material with a crosslinking agent, and delivering the medical device to a target tissue for releasing the drug and treating the tissue. The collagen-drug-genipin compound or the chitosan-drug-genipin compound and methods of manufacture as disclosed and supported in the below examples produce new and unexpected results and hence are unobvious from the prior art. The medical device can be a stent, a non-stent implant or prosthesis, or a percutaneous device such as a catheter, a wire, a cannula, an endoscopic instrument or the like for the intended drug slow release. Further, the medical device can be a biological device or a non-biological device. In a preferred aspect, the stent application with collagen-drug-genipin compound or the chitosan-drug-genipin compound comprises use in lymphatic vessel, gastrointestinal tract (including the various ducts such as hepatic duct, bile duct, pancreatic duct, etc.), urinary tract (ureter, urethra, etc.), and reproductive tract (i.e., uterine tube, etc.). In one aspect, the non-stent implant may comprise annuloplasty rings, heart valve prostheses, venous valve bioprostheses, orthopedic implants, dental implants, ophthalmology implants, cardiovascular implants, and cerebral implants. In another aspect of the present invention, the target tissue may comprise vulnerable plaque, atherosclerotic plaque, tumor or cancer, brain tissue, vascular vessel or tissue, orthopedic tissue, ophthalmology tissue or the like. The vulnerable plaque is the atherosclerotic plaque that is vulnerably prone to rupture in a patient.

In another embodiment of the present invention, it is disclosed a biological substance for treating tissue of a patient with drug slow release, wherein the biological substance is made of drug-containing biological material that may be solidifiable upon change of environmental condition(s) and is biocompatible after being crosslinked with a crosslinker, such as genipin, epoxy compounds, dialdehyde starch, dimethyl adipimidate, carbodiimide, glutaraldehyde, or the like.

In still another embodiment of the present invention, it is disclosed that a method for treating tissue of a patient comprising, in combination, mixing a drug with a biological material, chemically treating the drug with the biological material with a crosslinking agent, loading the drug-containing biological material onto an apparatus or medical device. In one preferred embodiment, the method further comprises a step of solidifying the drug-containing biological material.

It is some aspect of the present invention that the method may further comprise chemically linking the drug with the biological material through a crosslinker, wherein the drug comprises at least a crosslinkable functional group, for example, an amino group.

It is a further aspect of the prestent invention to provide a method for treating vascular restenosis comprising, in combination, loading a drug-containing biological material onto a medical device, chemically treating the drug-containing biological material with a crosslinking agent, and delivering the medical device to a vascular restenosis site for treating the vascular restenosis. In one embodiment, the method further comprises a step of solidifying the drug-containing biological material, wherein at least a portion of the biological material comprises a solidifiable substrate or material.

Drug for Use in Collagen-Drug-Genipin Compound

The drugs used in the current generation drug eluting cardiovascular stents include two major mechanisms: cytotoxic and cytostatic. Some aspects of the invention relating to the drugs used in collagen-drug-genipin compound from the category of cytotoxic mechanism comprise actinomycin D, paclitaxel, vincristin, methotrexate, and angiopeptin. Some aspects of the invention relating to the drugs used in collagen-drug-genipin compound from the category of cytostatic mechanism comprise batimastat, halofuginone, sirolimus, tacrolimus, everolimus, tranilast, dexamethasone, and mycophenylic acid (MPA). Some aspects of the prestent invention provide a bioactive agent in a bioactive agent-eluting device, wherein the bioactive agent is selected from a group consisting of actinomycin D, paclitaxel, vincristin, methotrexate, and angiopeptin, batimastat, halofuginone, sirolimus, tacrolimus, everolimus, tranilast, dexamethasone, and mycophenylic acid.

Everolimus with molecular weight of 958 (a chemical formula of $C_{53}H_{83}NO_{14}$) is poorly soluble in water and is a novel proliferation inhibitor. There is no clear upper therapeutic limit of everolimus. However, thrombocytopenia occurs at a rate of 17% at everolimus trough serum concentrations above 7.8 ng/ml in renal transplant recipients (Expert Opin Investig Drugs 2002; 11(12):1845-1857). In a patient, everolimus binds to cytosolic immunophyllin FKBP12 to inhibit growth factor-driven cell proliferation. Everolimus has shown promising results in animal studies, demonstrating a 50% reduction of neointimal proliferation compared with a control bare metal stent.

Straub et al. in U.S. Pat. No. 6,395,300 discloses a wide variety of drugs that are useful in the methods and compositions described herein, entire contents of which, including a variety of drugs, are incorporated herein by reference. Drugs contemplated for use in the compositions described in U.S. Pat. No. 6,395,300 and herein disclosed include the following categories and examples of drugs and alternative forms of these drugs such as alternative salt forms, free acid forms, free base forms, and hydrates:

analgesics/antipyretics (e.g., aspirin, acetaminophen, ibuprofen, naproxen sodium, buprenorphine, propoxyphene hydrochloride, propoxyphene napsylate, meperidine hydrochloride, hydromorphone hydrochloride, morphine, oxycodone, codeine, dihydrocodeine bitartrate, pentazocine, hydrocodone bitartrate, levorphanol, diflunisal, trolamine salicylate, nalbuphine hydrochloride, mefenamic acid, butorphanol, choline salicylate, butalbital, phenyltoloxamine citrate, diphenhydramine citrate, methotrimeprazine, cinnamedrine hydrochloride, and meprobamate);

antiasthamatics (e.g., ketotifen and traxanox);

antibiotics (e.g., neomycin, streptomycin, chloramphenicol, cephalosporin, ampicillin, penicillin, tetracycline, and ciprofloxacin);

antidepressants (e.g., nefopam, oxypertine, doxepin, amoxapine, trazodone, amitriptyline, maprotiline, phenylzine, desipramine, nortriptyline, tranylcypromine, fluoxetine, doxepin, imipramine, imipramine pamoate, isocarboxazid, trimipramine, and protriptyline);

antidiabetics (e.g., biguanides and sulfonylurea derivatives);

antifungal agents (e.g., griseofulvin, ketoconazole, itraconizole, amphotericin B, nystatin, and candicidin);

antihypertensive agents (e.g., propanolol, propafenone, oxyprenolol, nifedipine, reserpine, trimethaphan, phenoxybenzamine, pargyline hydrochloride, deserpidine, diazoxide, guanethidine monosulfate, minoxidil, rescinnamine, sodium nitroprusside, rauwolfia serpentina, alseroxylon, and phentolamine);

anti-inflammatories (e.g., (non-steroidal) indomethacin, ketoprofen, flurbiprofen, naproxen, ibuprofen, ramifenazone, piroxicam, (steroidal) cortisone, dexamethasone, fluazacort, celecoxib, rofecoxib, hydrocortisone, prednisolone, and prednisone);

antineoplastics (e.g., cyclophosphamide, actinomycin, bleomycin, daunorubicin, doxorubicin hydrochloride, epirubicin, mitomycin, methotrexate, fluorouracil, carboplatin, carmustine (BCNU), methyl-CCNU, cisplatin, etoposide, camptothecin and derivatives thereof, phenesterine, paclitaxel and derivatives thereof, docetaxel and derivatives thereof, vinblastine, vincristine, tamoxifen, piposulfan,);

antianxiety agents (e.g., lorazepam, buspirone, prazepam, chlordiazepoxide, oxazepam, clorazepate dipotassium, diazepam, hydroxyzine pamoate, hydroxyzine hydrochloride, alprazolam, droperidol, halazepam, chlormezanone, and dantrolene);

immunosuppressive agents (e.g., cyclosporine, azathioprine, mizoribine, and FK506 (tacrolimus));

antimigraine agents (e.g., ergotamine, propanolol, isometheptene mucate, and dichloralphenazone);

sedatives/hypnotics (e.g., barbiturates such as pentobarbital, pentobarbital, and secobarbital; and benzodiazapines such as flurazepam hydrochloride, triazolam, and midazolam);

antianginal agents (e.g., beta-adrenergic blockers; calcium channel blockers such as nifedipine, and diltiazem; and nitrates such as nitroglycerin, isosorbide dinitrate, pentaerythritol tetranitrate, and erythrityl tetranitrate);

antipsychotic agents (e.g., haloperidol, loxapine succinate, loxapine hydrochloride, thioridazine, thioridazine hydrochloride, thiothixene, fluphenazine, fluphenazine decanoate, fluphenazine enanthate, trifluoperazine, chlorpromazine, perphenazine, lithium citrate, and prochlorperazine);

antimanic agents (e.g., lithium carbonate);

antiarrhythmics (e.g., bretylium tosylate, esmolol, verapamil, amiodarone, encainide, digoxin, digitoxin, mexiletine, disopyramide phosphate, procainamide, quinidine sulfate, quinidine gluconate, quinidine polygalacturonate, flecainide acetate, tocainide, and lidocaine);

antiarthritic agents (e.g., phenylbutazone, sulindac, penicillanine, salsalate, piroxicam, azathioprine, indomethacin, meclofenamate, gold sodium thiomalate, ketoprofen, auranofin, aurothioglucose, and tolmetin sodium);

antigout agents (e.g., colchicine, and allopurinol);

anticoagulants (e.g., heparin, heparin sodium, and warfarin sodium);

thrombolytic agents (e.g., urokinase, streptokinase, and alteplase);

antifibrinolytic agents (e.g., aminocaproic acid);

hemorheologic agents (e.g., pentoxifylline);

antiplatelet agents (e.g., aspirin);

anticonvulsants (e.g., valproic acid, divalproex sodium, phenyloin, phenyloin sodium, clonazepam, primidone, phenobarbitol, carbamazepine, amobarbital sodium, methsuximide, metharbital, mephobarbital, mephenyloin, phensuximide, paramethadione, ethotoin, phenacemide, secobarbitol sodium, clorazepate dipotassium, and trimethadione);

antiparkinson agents (e.g., ethosuximide);

antihistamines/antipruritics (e.g., hydroxyzine, diphenhydramine, chlorpheniramine, brompheniramine maleate, cyproheptadine hydrochloride, terfenadine, clemastine fumarate, triprolidine, carbinoxamine, diphenylpyraline, phenindamine, azatadine, tripelennamine, dexchlorpheniramine maleate, methdilazine, and);

agents useful for calcium regulation (e.g., calcitonin, and parathyroid hormone);

antibacterial agents (e.g., amikacin sulfate, aztreonam, chloramphenicol, chloramphenicol palirtate, ciprofloxacin, clindamycin, clindamycin palmitate, clindamycin phosphate, metronidazole, metronidazole hydrochloride, gentamicin sulfate, lincomycin hydrochloride, tobramycin sulfate, vancomycin hydrochloride, polymyxin B sulfate, colistimethate sodium, and colistin sulfate);

antiviral agents (e.g., interferon alpha, beta or gamma, zidovudine, amantadine hydrochloride, ribavirin, and acyclovir);

antimicrobials (e.g., cephalosporins such as cefazolin sodium, cephradine, cefaclor, cephapirin sodium, ceftizoxime sodium, cefoperazone sodium, cefotetan disodium, cefuroxime azotil, cefotaxime sodium, cefadroxil monohydrate, cephalexin, cephalothin sodium, cephalexin hydrochloride monohydrate, cefamandole nafate, cefoxitin sodium, cefonicid sodium, ceforanide, ceftriaxone sodium, ceftazidime, cefadroxil, cephradine, and cefuroxime sodium; penicillins such as ampicillin, amoxicillin, penicillin G benzathine, cyclacillin, ampicillin sodium, penicillin G potassium, penicillin V potassium, piperacillin sodium, oxacillin sodium, bacampicillin hydrochloride, cloxacillin sodium, ticarcillin disodium, azlocillin sodium, carbenicillin indanyl sodium, penicillin G procaine, methicillin sodium, and nafcillin sodium; erythromycins such as erythromycin ethylsuccinate, erythromycin, erythromycin estolate, erythromycin lactobionate, erythromycin stearate, and erythromycin ethylsuccinate; and tetracyclines such as tetracycline hydrochloride, doxycycline hyclate, and minocycline hydrochloride, azithromycin, clarithromycin);

anti-infectives (e.g., GM-CSF);

bronchodilators (e.g., sympathomimetics such as epinephrine hydrochloride, metaproterenol sulfate, terbutaline sulfate, isoetharine, isoetharine mesylate, isoetharine hydrochloride, albuterol sulfate, albuterol, bitolterolmesylate, isoproterenol hydrochloride, terbutaline sulfate, epinephrine bitartrate, metaproterenol sulfate, epinephrine, and epinephrine bitartrate; anticholinergic agents such as ipratropium bromide; xanthines such as aminophylline, dyphylline, metaproterenol sulfate, and aminophylline; mast cell stabilizers such as cromolyn sodium; inhalant corticosteroids such as beclomethasone dipropionate (BDP), and beclomethasone dipropionate monohydrate; salbutamol; ipratropium bromide; budesonide; ketotifen; salmeterol; xinafoate; terbutaline sulfate; triamcinolone; theophylline; nedocromil sodium; metaproterenol sulfate; albuterol; flunisolide; fluticasone proprionate;

steroidal compounds and hormones (e.g., androgens such as danazol, testosterone cypionate, fluoxymesterone, ethylestosterone, testosterone enathate, methyltestosterone, fluoxymesterone, and testosterone cypionate; estrogens such as estradiol, estropipate, and conjugated estrogens; progestins such as methoxyprogesterone acetate, and norethindrone acetate; corticosteroids such as triamcinolone, betamethasone, betamethasone sodium phosphate, dexamethasone, dexamethasone sodium phosphate, dexamethasone acetate, prednisone, methylprednisolone acetate suspension, triamcinolone acetonide, methylprednisolone, prednisolone sodium phosphate, methylprednisolone sodium succinate, hydrocortisone sodium succinate, triamcinolone hexacetonide, hydrocortisone, hydrocortisone cypionate, prednisolone, fludrocortisone acetate, paramethasone acetate, prednisolone tebutate, prednisolone acetate, prednisolone sodium phosphate, and hydrocortisone sodium succinate; and thyroid hormones such as levothyroxine sodium);

hypoglycemic agents (e.g., human insulin, purified beef insulin, purified pork insulin, glyburide, chlorpropamide, glipizide, tolbutamide, and tolazamide);

hypolipidemic agents (e.g., clofibrate, dextrothyroxine sodium, probucol, pravastitin, atorvastatin, lovastatin, and niacin);

proteins (e.g., DNase, alginase, superoxide dismutase, and lipase);

nucleic acids (e.g., sense or anti-sense nucleic acids encoding any therapeutically useful protein, including any of the proteins described herein);

agents useful for erythropoiesis stimulation (e.g., erythropoietin);

antiulcer/antireflux agents (e.g., famotidine, cimetidine, and ranitidine hydrochloride);

antinauseants/antiemetics (e.g., meclizine hydrochloride, nabilone, prochlorperazine, dimenhydrinate, promethazine hydrochloride, thiethylperazine, and scopolamine);

as well as other drugs useful in the compositions and methods described herein include mitotane, halonitrosoureas, anthrocyclines, ellipticine, ceftriaxone, ketoconazole, ceftazidime, oxaprozin, albuterol, valacyclovir, urofollitropin, famciclovir, flutamide, enalapril, mefformin, itraconazole, buspirone, gabapentin, fosinopril, tramadol, acarbose, lorazepan, follitropin, glipizide, omeprazole, fluoxetine, lisinopril, tramsdol, levofloxacin, zafirlukast, interferon, growth hormone, interleukin, erythropoietin, granulocyte stimulating factor, nizatidine, bupropion, perindopril, erbumine, adenosine, alendronate, alprostadil, benazepril, betaxolol, bleomycin sulfate, dexfenfluramine, diltiazem, fentanyl, flecainid, gemcitabine, glatiramer acetate, granisetron, lamivudine, mangafodipir trisodium, mesalamine, metoprolol fumarate, metronidazole, miglitol, moexipril, monteleukast, octreotide acetate, olopatadine, paricalcitol, somatropin, sumatriptan succinate, tacrine, verapamil, nabumetone, trovafloxacin, dolasetron, zidovudine, finasteride, tobramycin, isradipine, tolcapone, enoxaparin, fluconazole, lansoprazole, terbinafine, pamidronate, didanosine, diclofenac, cisapride, venlafaxine, troglitazone, fluvastatin, losartan, imiglucerase, donepezil, olanzapine, valsartan, fexofenadine, calcitonin, and ipratropium bromide. These drugs are generally considered to be water soluble.

Preferred drugs useful in the prestent invention may include albuterol, adapalene, doxazosin mesylate, mometasone furoate, ursodiol, amphotericin, enalapril maleate, felodipine, nefazodone hydrochloride, valrubicin, albendazole, conjugated estrogens, medroxyprogesterone acetate, nicardipine hydrochloride, zolpidem tartrate, amlodipine besylate, ethinyl estradiol, omeprazole, rubitecan, amlodipine besylate/benazepril hydrochloride, etodolac, paroxetine hydrochloride, paclitaxel, atovaquone, felodipine, podofilox, paricalcitol, betamethasone dipropionate, fentanyl, pramipexole dihydrochloride, Vitamin $D_3$ and related analogues, finasteride, quetiapine fumarate, alprostadil, candesartan, cilexetil, fluconazole, ritonavir, busulfan, carbamazepine, flumazenil, risperidone, carbemazepine, carbidopa, levodopa, ganciclovir, saquinavir, amprenavir, carboplatin, glyburide, sertraline hydrochloride, rofecoxib carvedilol, clobustasol, diflucortolone, halobetasolproprionate, sildenafil citrate, celecoxib, chlorthalidone, imiquimod, simvastatin, citalopram, ciprofloxacin, irinotecan hydrochloride, sparfloxacin, efavirenz, cisapride monohydrate, lansoprazole, tamsulosin hydrochloride, mofafinil, clarithromycin, letrozole, terbinafine hydrochloride, rosiglitazone maleate, diclofenac sodium, lomefloxacin hydrochloride, tirofiban hydrochloride, telmisartan, diazapam, loratadine, toremifene citrate, thalidomide, dinoprostone, mefloquine hydrochloride, trandolapril, docetaxel, mitoxantrone hydrochloride, tretinoin, etodolac, triamcinolone acetate, estradiol, ursodiol, nelfinavir mesylate, indinavir, beclomethasone dipropionate, oxaprozin, flutamide, famotidine, nifedipine, prednisone, cefuroxime, lorazepam, digoxin, lovastatin, griseofulvin, naproxen, ibuprofen, isotretinoin, tamoxifen citrate, nimodipine, amiodarone, and alprazolam.

Specific non-limiting examples of some drugs that fall under the above categories include paclitaxel, docetaxel and derivatives, epothilones, nitric oxide release agents, heparin, aspirin, coumadin, PPACK, hirudin, polypeptide from angiostatin and endostatin, methotrexate, 5-fluorouracil, estradiol, P-selectin Glycoprotein ligand-1 chimera, abciximab, exochelin, eleutherobin and sarcodictyin, fludarabine, sirolimus, tranilast, VEGF, transforming growth factor (TGF)-beta, Insulin-like growth factor (IGF), platelet derived growth factor (PDGF), fibroblast growth factor (FGF), RGD peptide, beta or gamma ray emitter (radioactive) agents, and dexamethasone, tacrolimus, actinomycin-D, batimastat etc.

Sirolimus is a naturally occurring macrolide antibiotic produced by the fungus *Streptomyces* found in Easter Island. It was discovered by Wyeth-Ayerst in 1974 while screening fermentation products. Sirolimus with molecular weight of 916 (a chemical formula of $C_{51}H_{79}NO_{13}$) is non-water soluble and is a potential inhibitor of cytokine and growth factor mediated cell proliferation. FDA approved its use as oral immunosuppressive agents with a formulation of 2 to 5 mg/dose. The suggested drug-eluting efficacy is about 140 micrograms/cm$^2$, 95% drug release at 90 days and 30% drug-to-polymer ratio.

In some aspect of the prestent invention, the drug (also referred as a bioactive agent) may broadly comprise, but not limited to, synthetic chemicals, biotechnology-derived molecules, herbs, health food, extracts, and/or alternate medicines; for example, including allicin and its corresponding garlic extract, ginsenosides (for example, Rg1) and the corresponding ginseng extract, flavone/terpene lactone and the corresponding *ginkgo biloba* extract, glycyrrhetinic acid and the corresponding licorice extract, and polyphenyl/proanthocyanides and the corresponding grape seed extract.

While the preventive and treatment properties of the foregoing therapeutic substances, agents, drugs, or bioactive agents are well known to those having ordinary skill in the art, the substances or agents are provided by way of example and are not meant to be limiting. Other therapeutic substances are equally applicable for use with the disclosed methods, devices, and compositions.

In the prestent invention, the terms "crosslinking", "fixation", "chemical modification", and "chemical treatment" for tissue are used interchangeably.

FIG. 1 shows chemical structures of glutaraldehyde and genipin that are used in the chemical treatment examples of the current disclosure. Other crosslink agents may equally be applicable for collagen-drug-genipin and/or chitosan-drug-genipin compound disclosed herein.

Other than genipin and glutaraldehyde, the crosslinking agent that may be used in chemical treatment of the prestent invention may include formaldehyde, dialdehyde starch, glyceraldehydes, cyanamide, diimides, diisocyanates, dimethyl adipimidate, carbodiimide, and epoxy compound.

Figure 3:
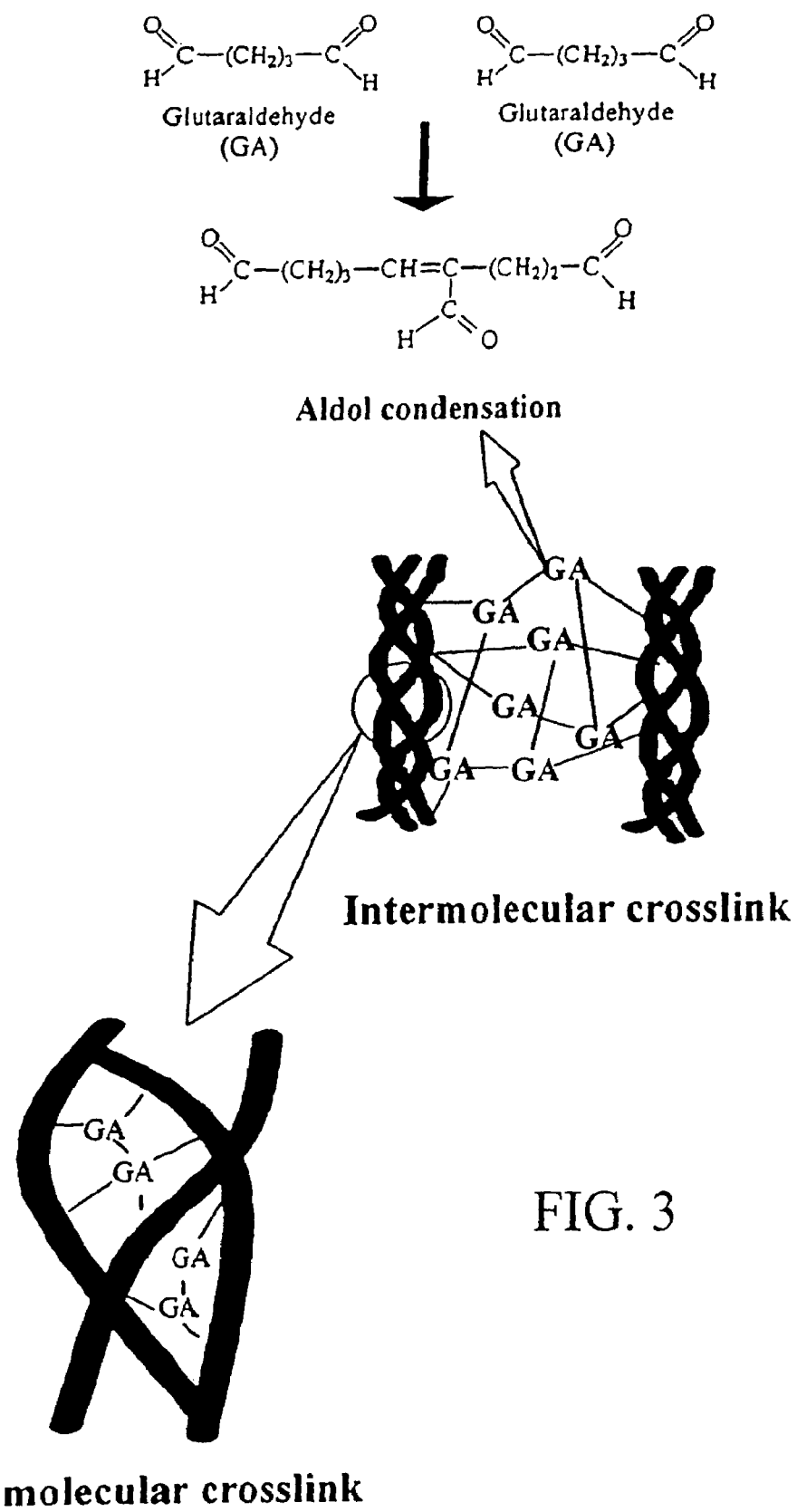
FIG. 3 is a proposed crosslinking mechanism for a crosslinker, glutaraldehyde (GA) with collagen intermolecularly and/or intramolecularly.

FIG. 3 shows a proposed crosslinking mechanism for a crosslinker, glutaraldehyde (GA) with collagen intermolecularly and/or intramolecularly.

Figure 4A:
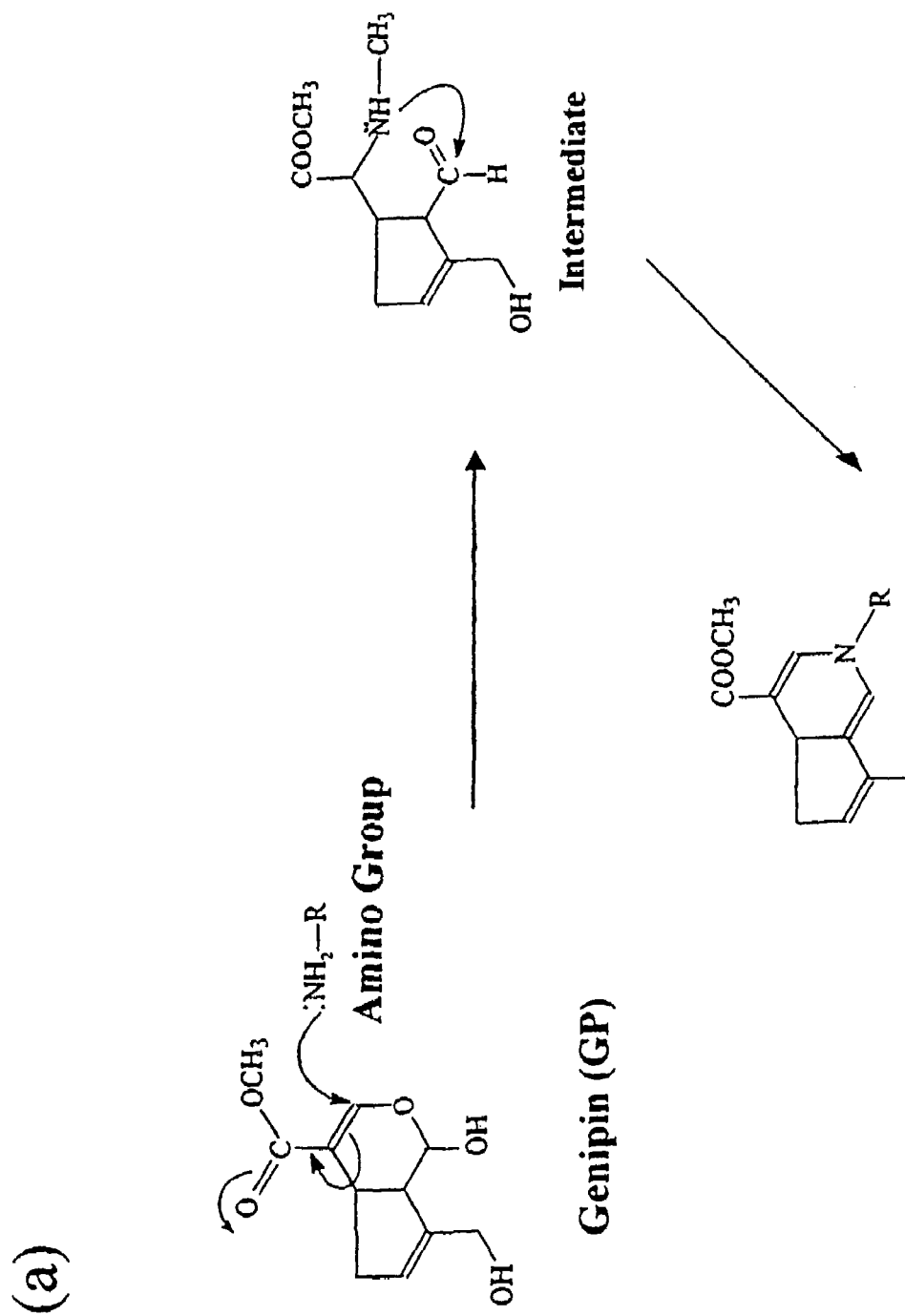
FIG. 4A is a proposed reaction mechanism between genipin and an amino group of a reactant, including collagen or certain type of drug of the prestent invention.
Figure 4B:
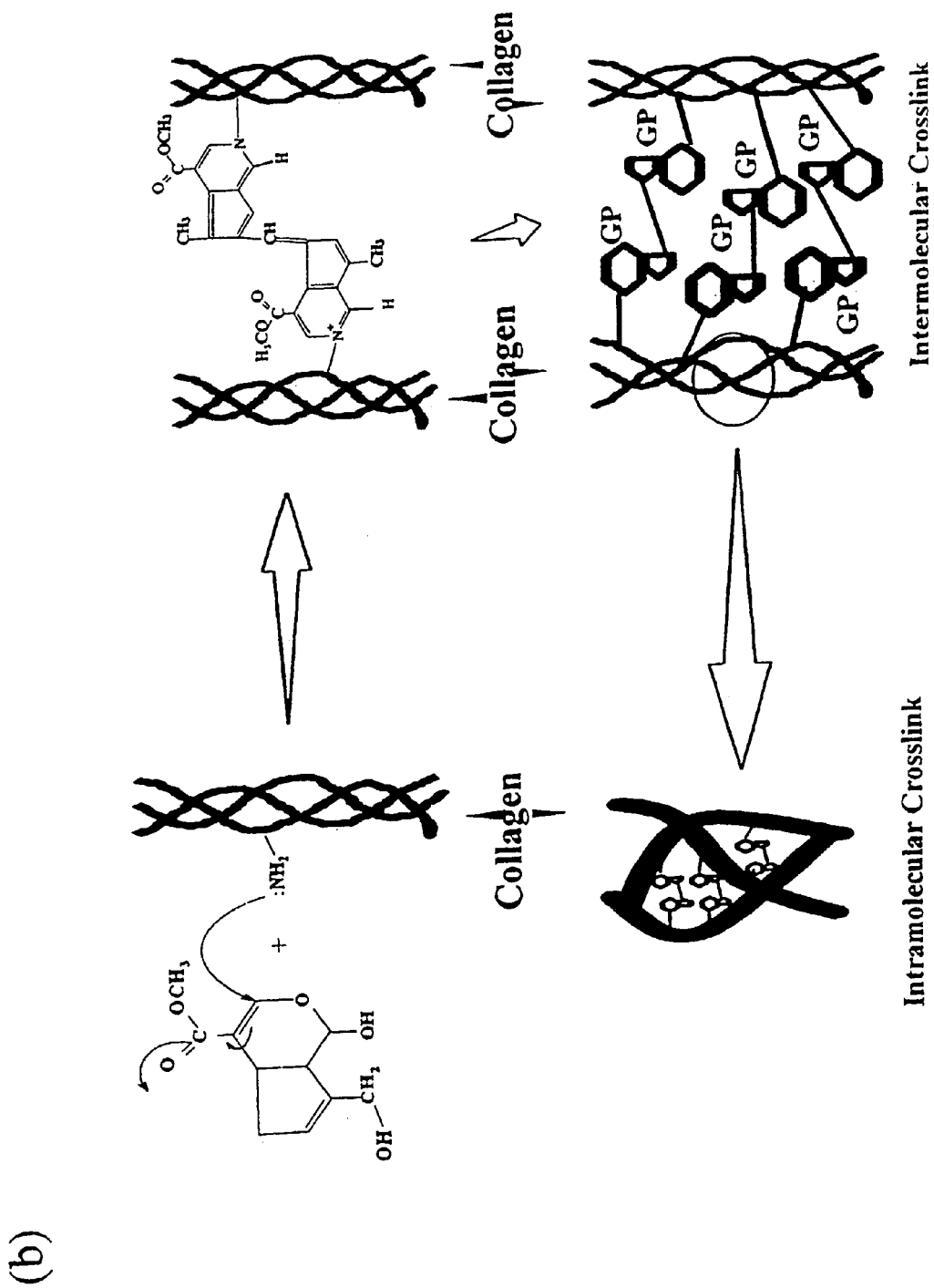
FIG. 4B is a proposed crosslinking mechanism for a crosslinker, genipin (GP) with collagen intermolecularly and/or intramolecularly.

FIG. 4A shows a proposed reaction mechanism between genipin and an amino group of a reactant, including collagen or certain type of drug of the prestent invention, while FIG. 4B shows a proposed crosslinking mechanism for a crosslinker, genipin (GP) with collagen intermolecularly and/or intramolecularly.

Figure 5:
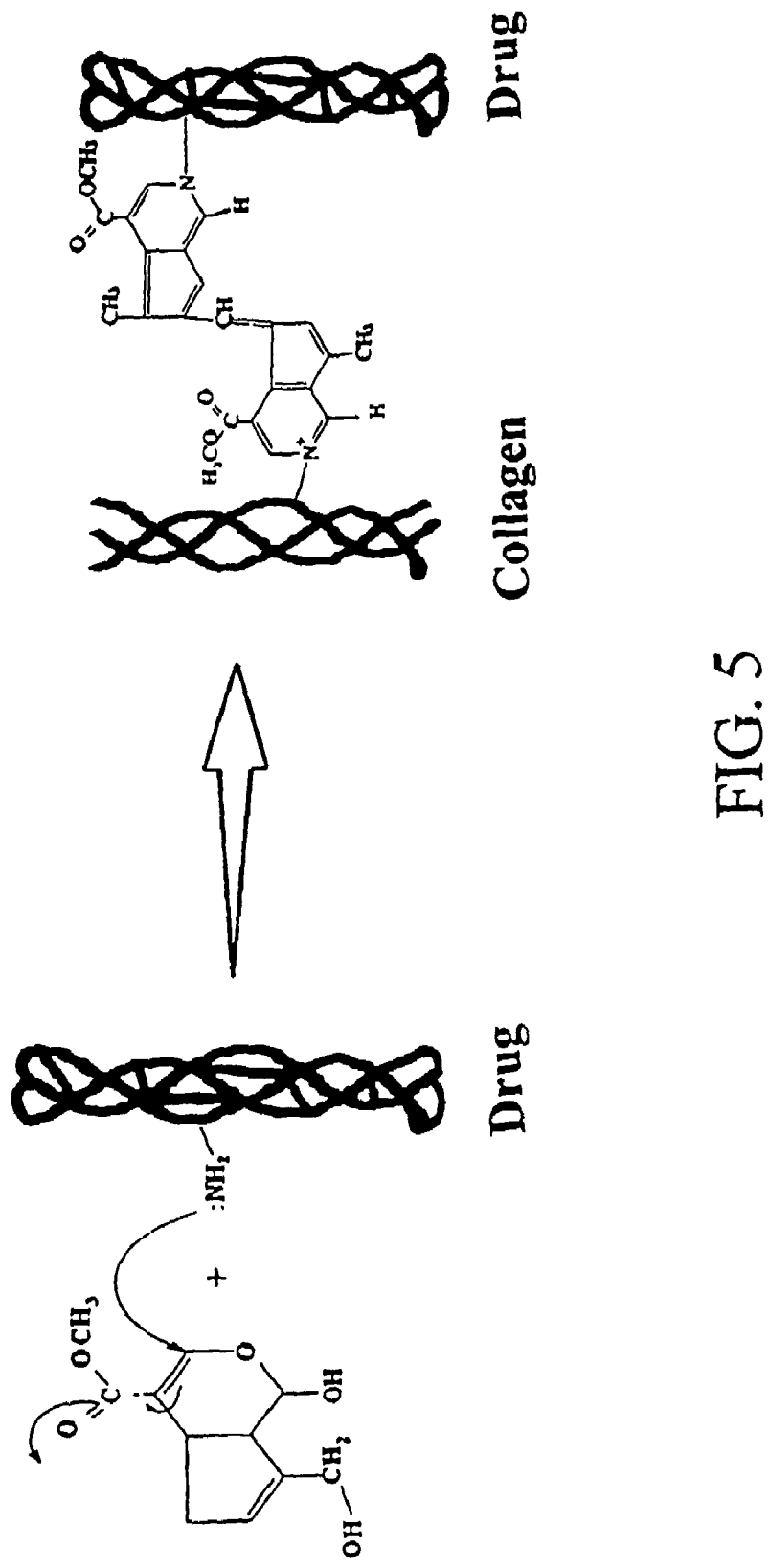
FIG. 5 is a schematic illustration for genipin to crosslink an amino-containing collagen and an amino-containing drug.
Figure 6:
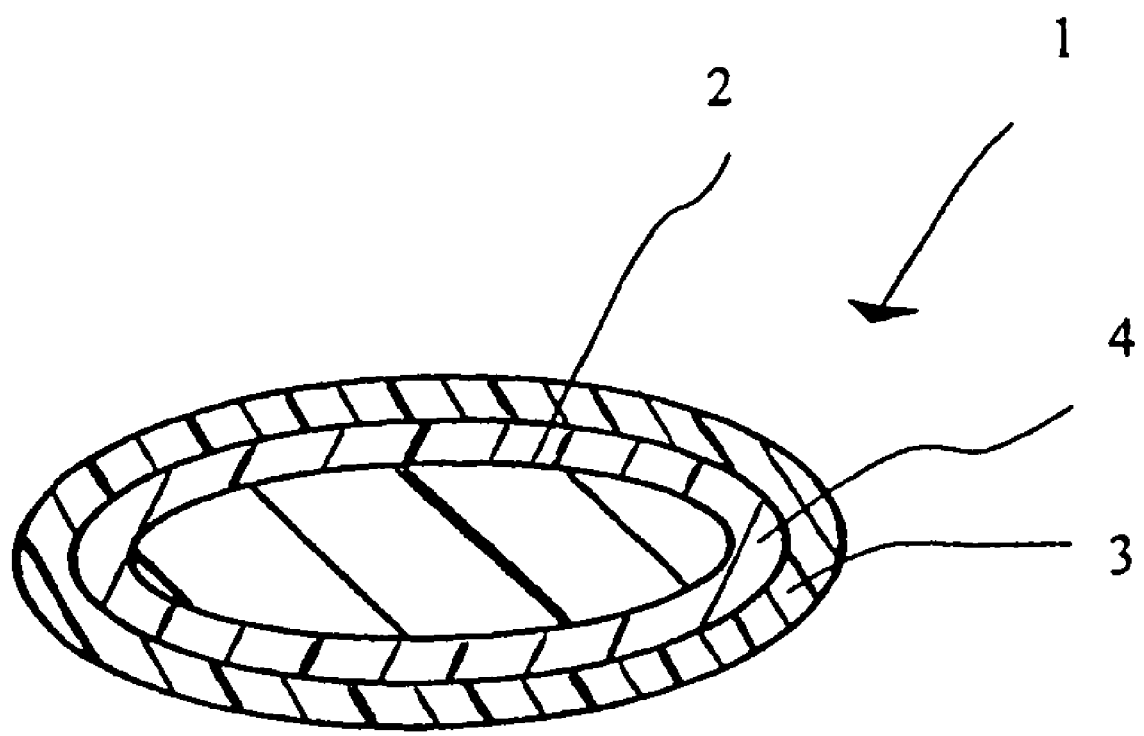
FIG. 6 is an illustrated example of a cross-sectional view for a vascular stent coated with drug-containing collagen crosslinked with genipin according to the principles of the prestent invention.
Figure 7:
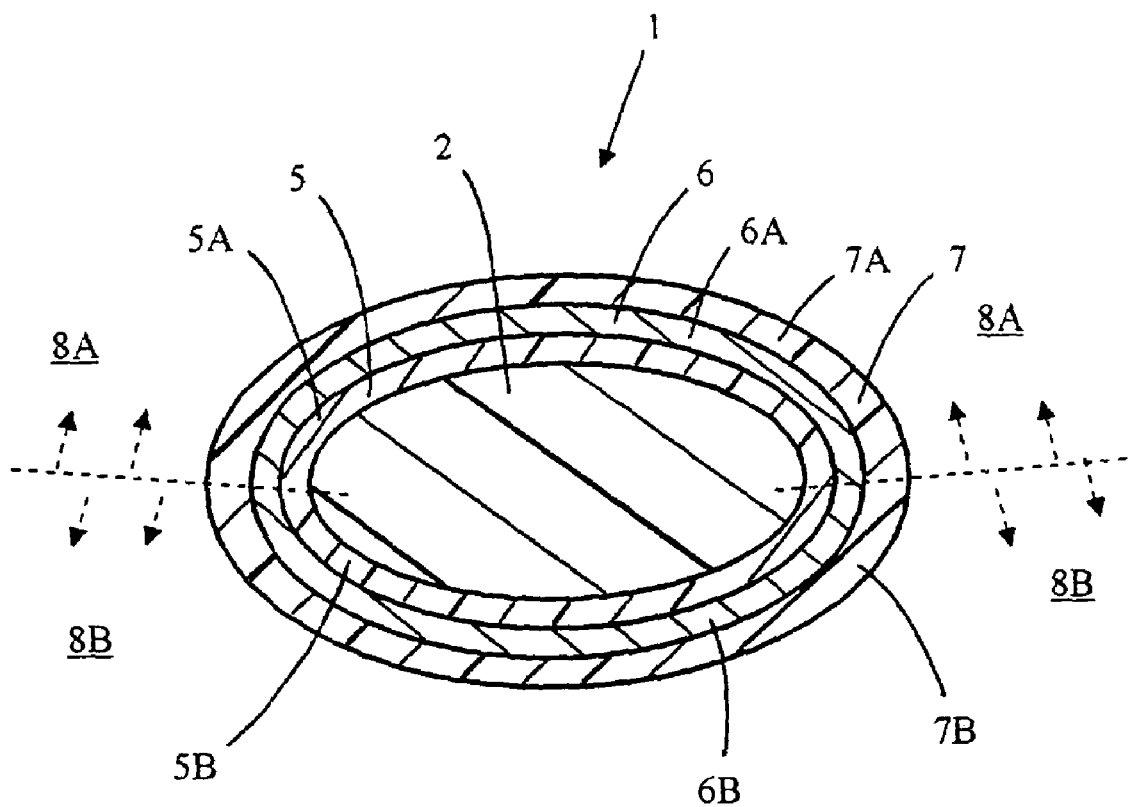
FIG. 7 is one embodiment of a cross-sectional view for a vascular stent coated with drug-containing collagen layers that are crosslinked with genipin.

FIG. 5 is a schematic illustration for genipin to crosslink an amino-containing collagen and an amino-containing drug. It is also conceivable for a crosslinker, such as genipin to link an amine-containing substrate and an amino-containing drug. An example of amine-containing substrate is polyurethane and the like.

Glutaraldehyde Crosslinking

Glutaraldehyde has been used extensively as a crosslinking agent for fixing biologic tissues. By means of its aldehyde functional groups, glutaraldehyde reacts primarily with the $\epsilon$-amino groups of lysyl or hydroxylysyl residues within biologic tissues. The mechanism of fixation of biologic tissues or biologic matrix with glutaraldehyde can be found elsewhere. Polymerization of glutaraldehyde molecules in aqueous solution with observable reductions in free aldehyde have been reported previously (Nimni M E et al. in Nimni M E, editor. COLLAGEN. Vol. III. Boca Raton (Fla.); CRC Press 1998. pp. 1-38). In polymerization the aldehyde functional groups of 2 glutaraldehyde molecules may undergo an aldol condensation (FIG. 3). With glutaraldehyde polymerization, subsequent to fixation, a network crosslinking structure could conceivably be created intramolecularly and intermolecularly within collagen fibers (FIG. 3).

It is conceivable that a substance (for example, a drug) having an amine or amino functional group may react with glutaraldehyde as illustrated above. By combining collagen, glutaraldehyde and a drug having an amine or amino group, the crosslinked compound may link collagen to the drug via glutaraldehyde as a crosslinker.

Crosslinking of A Polymer Having an Amine Group

Several biocompatible plastic polymers or synthetic polymers have one or more amine group in their chemical structures. The amine group may become reactive toward a crosslinker, such as glutaraldehyde, genipin or epoxy compounds. Therefore, it is conceivable that by combining a polymer having an amine group, glutaraldehyde and a drug having at least an amine or amino group, the crosslinked compound may have the polymer linked to the drug via glutaraldehyde as a crosslinker. Other crosslinkers are also applicable.

Genipin Crosslinking

It was found by Sung H W (Biomaterials 1999; 20:1759-72) that genipin can react with the free amino groups of lysine, hydroxylysine, or arginine residues within biologic tissues. A prior study reports that the structures of the intermediates, leading to a blue pigment produced from genipin and methylamine, the simplest primary amine. The mechanism was suggested that the genipin-methylamine monomer is formed through a nucleophilic attack by methylamine on the olefinic carbon at C-3 of genipin, followed by opening of the dihydropyran ring and attack by the secondary amino group on the resulting aldehyde group (FIG. 4A). The blue-pigment was thought formed through oxygen radical-induced polymerization and dehydrogenation of several intermediary pigments.

As disclosed by Sung H W (J Thorac Cardiovasc Surg 2001; 122:1208-1218), the simplest component in the blue pigment was a 1:1 adduct. It was suggested that genipin reacts spontaneously with an amino acid to form a nitrogen iridoid, which undergoes dehydration to form an aromatic monomer. Dimerization occurs at the second stage, perhaps by means of radical reaction. The results suggest that genipin may form intramolecular and intermolecular crosslinks with cyclic structure within collagen fibers in biologic tissue (FIG. 4B) or solidifiable collagen-containing biological material.

It is disclosed herein that genipin is capable of reacting with a drug having an amine or amino group. By combining collagen (or a biological material or matrix), genipin and the drug having an amine or amino group, the crosslinked compound may have collagen linked to the drug via genipin as a bridge crosslinker (FIG. 5).

As disclosed and outlined in the co-pending patent application Ser. No. 10/067,130 filed Feb. 4, 2002, entitled "Acellular biological material chemically treated with genipin" by one of the prestent inventors, the degrees in inflammatory reaction in the animal studies for the genipin-fixed cellular and acellular tissue were significantly less than their glutaraldehyde-fixed counterparts. Additionally, it was noted that the inflammatory reactions for the glutaraldehyde-fixed cellular and acellular tissue lasted significantly longer than their genipin-fixed counterparts. These findings indicate that the biocompatibility of the genipin-fixed cellular and acellular tissue is superior to the glutaraldehyde-fixed cellular and acellular tissue. It is hypothesized that the lower inflammatory reactions observed for the genipin-fixed cellular and acellular tissue may be due to the lower cytotoxicity of their remaining residues, as compared to the glutaraldehyde-fixed counterparts. In a previous study, it was found that genipin is significantly less cytotoxic than glutaraldehyde (J Biomater Sci Polymer Edn 1999; 10:63-78). The cytotoxicity observed for the glutaraldehyde-fixed cellular and acellular tissue seems to result from a slow leaching out of unreacted glutaraldehyde as well as the reversibility of glutaraldehyde-crosslinking. It was observed that when concentrations above 0.05% glutaraldehyde were used to crosslink materials, a persistent foreign-body reaction occurred (J Biomater Sci Polymer Edn 1999; 10:63-78).

Some aspects of the invention related to genipin-crosslinked gelatin as a drug carrier. In one embodiment, it is provided a method for treating tissue of a patient comprising, in combination, loading a solidifiable drug-containing gelatin onto an apparatus or medical device, solidifying the drug-containing gelatin, chemically treating the gelatin with a crosslinking agent, and delivering the medical device to the tissue for treating the tissue. Gelatin microspheres haven been widely evaluated as a drug carrier. However, gelatin dissolves rather rapidly in aqueous environments, making the use of gelatin difficult for the production of long-term drug delivery systems. Hsing and associates reported that the degradation rate of the genipin-crosslinked microspheres is significantly increased (J Biomed Mater Res 2003; 65A:271-282).

EXAMPLE #1

Dissolve chitosan powder in acetic acid at about pH 4. Chitosan (MW: about 70,000) was purchased from Fluka Chemical Co. of Switzerland. The deacetylation degree of the chitosan used was approximately 85%. Subsequently, adjust the chitosan solution to approximately pH 5.5 (right before it becomes gelled) with NaOH. Add in drug(s) of interest into the chitosan solution. While loading the drug-containing chitosan onto a stent, adjust the environment to pH 7 with NaOH to solidify the chitosan onto the stent. The process can be accomplished via a continuous assembly line step by providing gradually increasing pH zones as the device passes by. It is further treated with a crosslinking agent, for example genipin to enhance the biodurability and biocompatibility. Note that the chemical formula for chitosan can be found in Mi F L, Tan Y C, Liang H F, and Sung H W, "*In vivo biocompatibility and degradability of a novel injectable-chitosan based implant.*" Biomaterials 2002; 23:181-191.

EXAMPLE #2

Add at least one drug of interest into a collagen solution at 4° C. While loading the drug-containing collagen onto a stent, adjust the environment temperature to about 37° C. to solidify the collagen onto the stent. The process can be accomplished via a continuous assembly line step by providing gradually increasing temperature zones as the device passes by. The loading step can be repeated a few times to increase the thickness or total quantity of the drug-containing collagen. The loading step can be started with a high-does drug-containing collagen and then loaded with a lower dose drug-containing collagen or vice versa. It is further treated with a crosslinking agent, for example genipin to enhance the biodurability and biocompatibility. The fixation details could be found elsewhere by Sung et al. (Sung H W, Chang Y, Liang I L, Chang W H and Chen Y C. "*Fixation of biological tissues with a naturally occurring crosslinking agent: fixation rate and effects pf pH, temperature, and initial fixative concentration.*" J Biomed Mater Res 2000; 52:77-87).

EXAMPLE #3

Add drug and stent in a NOCC solution at room temperature. The NOCC (named after "Nitrogen Oxygen carboxylmethyl chitosan") is a chitosan derived compound that is pH sensitive and can be used in drug delivery. This NOCC is water soluble at pH 7. Crosslink the NOCC and drug onto the stent by a crosslinking agent, for example genipin. This is a step of solidification. In one aspect of the prestent invention, after crosslinking, the drug containing NOCC can be made harder or more solid-like, if needed, by low pH at about 4. The finished stent slowly releases drug when in the body at a pH around neutral.

EXAMPLE #4

Taxol (paclitaxel) is practically water insoluble as some other drugs of interest in this disclosure. Therefore, first mechanically disperse paclitaxel in a collagen solution at about 4° C. Load the drug containing collagen onto a stent and subsequently raise the temperature to about 37° C. to solidify collagen fibers on the stent. The loading step may repeat a plurality of times. Subsequently, crosslink the coated stent with aqueous genipin. The crosslinking on the drug carrier, collagen or chitosan, substantially modify the drug diffusion or eluting rate depending on the degree of crosslinking.

EXAMPLE #5

Taxol (paclitaxel) is practically water insoluble as some other drugs of interest in this disclosure. Therefore, first mechanically disperse paclitaxel in a collagen solution at about 4° C. Load the drug containing collagen onto a stent and subsequently raise the temperature to about 37° C. to solidify collagen fibers on the stent. The loading may comprise spray coating, dip coating, plasma coating, painting or other known techniques. The loading step may repeat a plurality of times. The crosslinking on biological material (i.e., the drug carrier, collagen or chitosan,) substantially modify the drug diffusion or eluting rate depending on the degree of crosslinking, wherein the degree of crosslinking of the biological material at a first portion of the stent is different from the degree of crosslinking of the biological material at a second portion or at a third portion of the stent.

EXAMPLE #6

Sirolimus is used as a bioactive agent in this example. First mechanically disperse sirolimus in a collagen solution at about 4° C. Load the sirolimus containing collagen onto a stent and subsequently raise the temperature to about 37° C. to solidify collagen fibers on the stent. The loading may comprise spray coating, dip coating, plasma coating, painting or other known techniques. The loading step may repeat a plurality of times, wherein each loading step is followed by a crosslinking step, wherein each crosslinking step is either with esstentially the same crosslinking degree or with substantially different crosslinking degree. In one alternate embodiment, the degree of crosslinking of collagen at a first portion of the stent is different from the degree of crosslinking of collagen at a second portion of the stent. The resulting sirolimus containing stent with chemically crosslinked collagen is sterilized and packaged for clinical use. By way of example, one preferred sterilization condition may comprise 0.2% peracetic acid and 4% ethanol at room temperature for a period of 1 minute to a few hours.

Some aspects of the invention provide a medical device, comprising: an apparatus having a surface; a bioactive agent; and biological material loaded onto at least a portion of the surface of the apparatus, the biological material comprising the bioactive agent, wherein the biological material is thereafter crosslinked with a crosslinking agent. The medical device of the invention is further sterilized with a condition comprising a steriliant of peracetic acid about 0.1 to 5% and alcohol (preferably ethanol) about 1 to 20% at a temperature of 5 to 50° C. for a time of about 1 minute to 5 hours.

EXAMPLE #7

A collagen solution is used to dip or spray coat a coronary stent to evaluate the effect of the solution surface tension on coating uniformity. A control collagen solution at 10 mg/ml is used to dip coat a stainless steel stent at room temperature. Due to its high surface tension, the collagen tends to cluster or accumulate at the stent corner (where two struts meet) in a thin film. Even after the drying or solidifying step, the collagen at the stent corner is still disproportionately thicker than that at the linear strut portion. In a second experiment, a surfactant (surface tension reducing agent) of 1 μl octanol is added to the control collagen solution. The resulting collagen coated stent shows less cluster at the stent corner than the control run.

The cohesive forces between liquid molecules are responsible for the phenomenon known as surface tension. The molecules at the surface do not have other like molecules on all sides of them and consequently they cohere more strongly to those directly associated with them on the surface. This forms a surface "film" which makes it more difficult to move an object through the surface than to move it when it is completely submersed. Surface tension is typically measured using contact angle techniques in dynes/cm, the force in dynes required to break a film of length 1 cm. Equivalently, it can be stated as surface energy in ergs per square centimeter. Water at 20° C. has a surface tension of 72.8 dynes/cm compared to 22.3 for ethyl alcohol and 465 for mercury. Some aspects of the invention provide a method to load the solidifiable biological material onto at least a portion of a surface of a medical device comprising reducing surface tension of the biological material, wherein the step of loading comprises dip coating, spray coating, co-extrusion, co-molding, plasma coating, or the like.

The "biological substance" made of drug-containing biological material of the prestent invention and/or the collagen-drug-genipin compound on a stent can be sterilized before use by lyophilization, ethylene oxide sterilization, or sterilized in a series of ethanol solutions, with a gradual increase in concentration from 20% to 75% over a period of several hours. Finally, the drug-loaded stents are rinsed in sterilized saline solution and packaged. The drug carrier, collagen and chitosan, may be fully or partially crosslinked. In one aspect of the prestent invention, a partially crosslinked collagen/chitosan is biodegradable or bioerodible for drug slow-release.

FIG. 6 shows an illustrated example of a cross-sectional view for a medical device of a vascular stent 1 coated with drug-containing collagen 3 crosslinked with genipin according to the principles of the prestent invention. The stent is generally a mesh type tubular prosthesis made of stainless steel, Nitinol, gold, other metals or plastic material. The vascular stent 1 or a stent strut 2 for non-vascular application may further comprise another layer 4 which is slightly different in composition from the drug-containing collagen layer 3. In some aspect, the layer 4 may have higher drug loading and higher adhesive properties enabling the layer to be securely coated onto the stent strut 2 or the medical device. Due to the barrier properties of the crosslinked collagen, drug could only slowly diffuse out of the crosslinked matrix or released along with biodegraded collagen. This type of drug-eluting stent having collagen carrier chemically treated with genipin is particularly useful in coronary stenting.

Special features for the drug-containing collagen adhesive layer 4 may be characterized by: the layer 4 is securely adhered onto the stent strut; drug is tightly loaded for drug slow release in weeks or months; and collagen is partially crosslinked or fully crosslinked by genipin for stability.

Special features for the drug-containing collagen layer 3 may be characterized by: the layer 3 is securely adhered to layer 4 and vice versa; and drug may be less tightly loaded or collagen may be crosslinked at a lower degree of crosslinkage for drug slow release in days or weeks.

Special features for the drug-loaded collagen and/or drug-loaded chitosan crosslinked by genipin may be characterized by: the crosslinked collagen/chitosan with interpenetrated drug enables drug diffusion at a controlled rate; collagen is tissue-friendly and flexible in deployment; and a crosslinked collagen/chitosan material enhances biocompatibility and controlled biodegradability. The whole process for manufacturing a collagen-drug-genipin or chitosan-drug-genipin compound can be automated in an environmentally controlled facility. Sufficient amount of collagen or drug could be loaded to the exterior side of the stent strut for restenosis mitigation or other therapeutic effects.

FIG. 7 shows one embodiment of a cross-sectional view for a vascular stent 1 with a stent strut 2, wherein the stent surface is coated with a plurality of drug-containing collagen layers 5, 6, 7 that are crosslinked with a crosslinker, or by ultraviolet irradiation or dehydrothermal treatment. FIG. 7 shows the stent outermost surface that is approximately categorized as the tissue contact surface section 8A upon implantation and the blood contact surface section 8B. In one embodiment, the layer thickness of the drug-containing collagen layers 5, 6, 7 in the tissue contact side (that is, 5A, 6A, and 7A) may be different from the layer thickness in the blood contact side (that is, 5B, 6B, and 7B). In another embodiment, there may comprise either none or at least one collagen layer in the blood contact side. Further, the total drug content, drug type, or drug concentration of the drug-containing collagen layers 5, 6, 7 in the tissue contact side (that is, 5A, 6A, and 7A) may be different from the total drug content, drug type, or the drug concentration in the blood contact side (that is, 5B, 6B, and 7B), respectively. In still another embodiment, each of the crosslinking degrees of the drug-containing collagen layers 5, 6, 7 in the tissue contact side (that is, 5A, 6A, and 7A) may be different from the crosslinking degree of the corresponding layer in the blood contact side (that is, 5B, 6B, and 7B).

EXAMPLE #8

Paclitaxel is used as a bioactive agent in this example. First step is to prepare a paclitaxel solution (Solution A) by mixing 20 mg paclitaxel in one ml absolute alcohol. The second step is to add Solution A into collagen solution by adjusting to a final pH4 to obtain Solution B, which has a paclitaxel concentration at about 4 mg/ml. Load the paclitaxel containing collagen onto a stent at room temperature and subsequently raise the collagen pH to about 7 to solidify collagen fibers on the stent. The loading may comprise spray coating, dip coating, plasma coating, painting or other known techniques. The loading may comprise a plurality of steps and forms a plurality layers, such as layers 5, 6, 7 in FIG. 7. Each loading step or layer is followed by a crosslinking step, wherein each crosslinking step is either with esstentially the same crosslinking degree or with substantially different crosslinking degree. In another embodiment, the total drug content, drug type, or the drug concentration in each loading step may be the same or different from each other depending on the clinical needs. In still another embodiment, the drug amount, drug type, or drug concentration loaded onto each layer may be different depending on the clinical needs. By way of examples, a coronary stent may comprise an outermost layer with anti-thrombogenic agent (for example, heparin, coumadin and the like) to mitigate acute thrombosis concerns, a middle layer with anti-proliferation agent to prevent sub-acute restenosis issues (for example, paclitaxel, everolimus, sirolimus, angiopeptin and the like) or anti-inflammatory agent, and an innermost layer with growth factors or angiogenesis agent to promote chronic endothelialization at the blood vessel lumen. The anti-inflammatory agent may comprise aspirin, lipid lowering statins, fat lowering lipostabil, estrogen and progestin, endothelin receptor antagonist, interleukin-6 antagonist or monoclonal antibodies to VCAM or ICAM.

Lipostabil is phosphatidylcholine, a liquid form of lecithin, an enzyme which occurs naturally in the body. It was first used in the 1950s to dial down climbing cholesterol and triglyceride numbers and is approved for use in Brazil, Germany, Italy and South America. It took Brazilian dermatologist, Patricia Rittes, widely credited with pioneering the treatment often called Lipo-Dissolve, to reincarnate the drug as a pathway to physical perfection. After experimental use as an injectable fat-dissolver by doctors overseas such as Rittes, it started to make its way stateside. Thanks to some anecdotal evidence and off label usage, a few doctors in the United States are now injecting surgery-shy but eager patients in order to send their eye bags packing, whittle pudgy upper arms and reduce other areas often too small to treat with liposuction. A patient gets injected with the drug at the trouble site or sites spaced over the course of several weeks. A topical anesthetic is used at the injection site. Then the patient waits a couple of weeks and goes back in for another round of shots. After the treatments are over and the swelling subsides, one should find a new, fat free area in its wake thanks to the fat dissolving properties of the drug.

Lipostabil is best used for small areas. Some aspects of the invention provide a method for treating a target tissue of vulnerable plaque of a patient, comprising: providing a medical device having a biodegradable apparatus, wherein a biological material loaded onto at least a portion of the surface of the apparatus, the biological material comprising at least one bioactive agent of lipostabil or fat dissolving agent; crosslinking the biological material with a crosslinking agent or with ultraviolet irradiation; and delivering the medical device to the target tissue of vulnerable plaque and releasing the bioactive agent for treating the target tissue. In one embodiment, the degradation rate of the biodegradable apparatus is slower than the degradation rate of the crosslinked biological material. In this case, the therapeutic effects of the bioactive agent goes along with the degradation of the partially crosslinked biological material prior to complete degradation of the biodegradable apparatus. In another embodiment, the degradation rate of the biodegradable apparatus is faster than the degradation rate of the crosslinked biological material. Under the conditions that the partially crosslinked biological material with its entrapped bioactive agent penetrates into the surrounding tissue, the earlier degradation of the biodegradable apparatus makes the lumen surface susceptible for re-endothelialization.

Vulnerable plaque (also known as high-risk plaque, dangerous plaque or unstable plaque) is the atherosclerotic plaque that is vulnerably prone to rupture. The vulnerable plaques also identify all thrombosis-prone plaques and plaques with a high probability of undergoing rapid progression, thus becoming culprit plaques. In most cases, vulnerable plaque is characterized by active inflammation, thin cap with large lipid core, endothelial denudation with superficial platelet aggression, fissured plaque, little vessel narrowing, and other factors. Some aspects of the invention provides a biodegradable stent loaded with at least one bioactive agent having partially crosslinked collagen carrier to treat the vulnerable plaque, wherein the bioactive agent is slow-released in an effective rate over an effective period of time to treat the inflammation or lipid core associated with vulnerable plaque.

EXAMPLE #9

Paclitaxel is used as a bioactive agent in this example. Other bioactive agent, such as sirolimus, everolimus, tacrolimus, dexamethasone, ABT-578, paclitaxel, and the like, may substitute for paclitaxel. First step is to prepare a paclitaxel solution (Solution A) by mixing 20 mg paclitaxel in one ml absolute alcohol. The second step is to add 0.15 ml of Solution A and 0.6 ml of 0.5% genipin solution into 4 mg/ml collagen solution by adjusting to a final pH4 to obtain Solution C at a spraying coatable condition, which has a paclitaxel concentration at about 4 mg/ml. Load the paclitaxel containing collagen onto a stent at about 30° C. temperature and subsequently leave the coated stent at 37° C. for a couple of days to solidify, evaporate acetic acid, and crosslink collagen on the stent. The loading may comprise spray coating, dip coating, plasma coating, painting or other known techniques. The loading step may repeat a plurality of times, wherein each loading step is followed by a crosslinking step, and wherein each crosslinking step is either with esstentially the same crosslinking degree or with substantially different crosslinking degree. The resulting drug containing stent with chemically crosslinked collagen is sterilized and packaged for clinical use. By way of example, on preferred sterilization condition may comprise 0.2% peracetic acid and 4% ethanol at room temperature for a period of 1 minute to a few hours. Another sterilization method may comprise a conventional ethylene oxide sterilization that is well known to ordinary persons skilled in the art.

Figure 8:
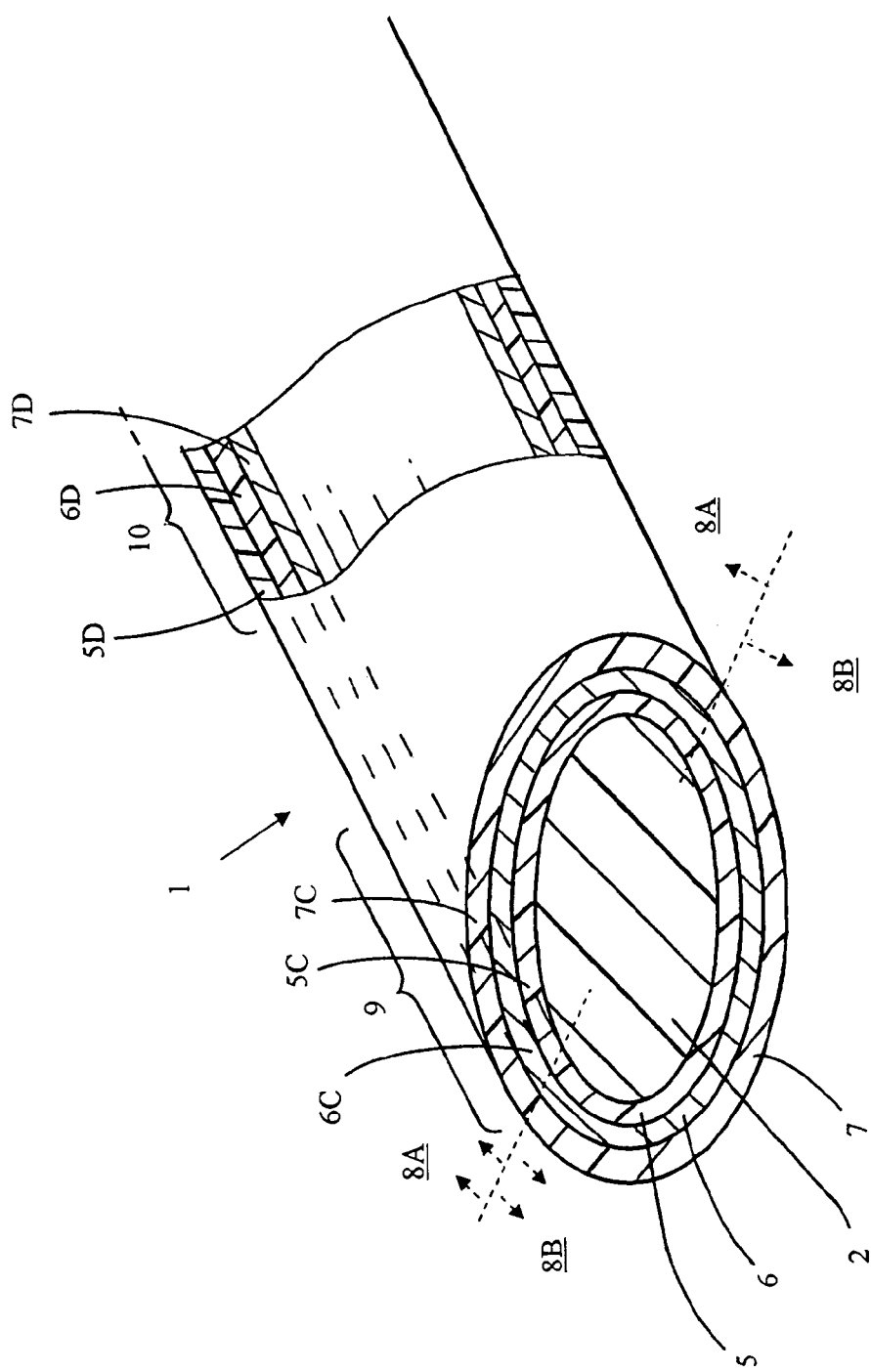
FIG. 8 is another embodiment of a longitudinal view for a vascular stent coated with drug-containing collagen layers that are crosslinked with genipin.

In one alternate embodiment, the crosslinking degree of collagen at a first portion (for example, at a portion 9 adjacent to an end) of the stent is different from the degree of crosslinking of collagen at a second portion (for example, at a second portion 10 spaced away from the end of the first portion 9) of the stent. The stent surface may comprise a first portion, a second portion and other portions, wherein the portion is defined as a surface area of interest, regardless of its size, shape, and location. FIG. 8 shows one embodiment of a longitudinal view for a vascular stent 1 with a stent strut 2, wherein the stent surface is coated with a plurality of drug-containing collagen layers 5, 6, 7 that are crosslinked with a crosslinker, or with ultraviolet irradiation or dehydrothermal treatment. FIG. 8 shows the stent surface or the collagen layer surface that is approximately categorized as the tissue contact surface section 8A upon implantation and the blood contact surface section 8B. In one embodiment, the layer thickness of the drug-containing collagen layers 5, 6, 7 in the first portion 9 (that is, 5C, 6C, and 7C) may be different from the layer thickness in the second portion 10 (that is, 5D, 6D, and 7D). In another embodiment, there may comprise either none or at least one collagen layer in the first portion 9 or the second portion 10. Further, the total drug content, drug type, or drug concentration of the drug-containing collagen layers 5, 6, 7 in the first portion 9 (that is, 5C, 6C, and 7C) may be different from the total drug content, drug type, or drug concentration in the second portion (that is, 5D, 6D, and 7D), respectively. In still another embodiment, each of the crosslinking degree of the drug-containing collagen layers 5, 6, 7 in the first portion (that is, 5C, 6C, and 7C) may be different from the crosslinking degree of the corresponding layer in the second portion (that is, 5D, 6D, and 7D), respectively.

Multi-Layer Drug Loading

Some aspects of the invention provide a drug-eluting implant (for example, a stent) comprising at least one collagen layer (with some or esstentially no bioactive agents) that is at least partially crosslinked and at least one drug-containing layer (with some or esstentially no collagen or "biological material"). The drug containing layer may contain certain inactive ingredient, such as fillers, diluents, or slow release media, such as biodegradable polymers. The following example illustrates one preferred embodiment for making multi-layer drug-loaded stent. In a further embodiment, different drug may be employed in each drug containing layer.

EXAMPLE #10

Sirolimus is used as a bioactive agent in this example. Other bioactive agent, such as everolimus, tacrolimus, dexamethasone, ABT-578, paclitaxel, and the like, may substitute for sirolimus. First, dissolve sirolimus in anhydride ethanol at a concentration about 500 μg/ml (coded as Solution X). Second, prepare collagen solution at a concentration about 5 mg/ml with a pH around 4 that is adjusted by acetic acid (coded as Solution Y). Then load (by spray coating or the like techniques) Solution X onto a rotating stent, followed by another step of loading Solution Y alternately. Each loading step may be separated by appropriate time duration sufficient to maintain certain integrity of the prior layer. In one embodiment, certain degree of mixing or penetrating between layers is desirable. A typical operating condition is for the stent on a horizontal mandrill to rotate at about 144 RPM. After at least one Solution X layer and at least one Solution Y layer are loaded onto a stent, spray a crosslinking solution (coded as Solution Z) by mixing 5% genipin in 70% ethanol for sufficient amount and spraying time, say from a few seconds to several minutes. Thereafter, leave the stent in a moderate temperature (around 37° C.), high humidity environment (close to about 100% relative humidity) for enough time (several minutes to several days) to partially crosslink the collagen portion on the stent. The stent would be ready for use after removing the residuals and sterilization.

Some aspects of the invention provide a drug-eluting stent comprising at least one drug-loaded collagen layer that is at least partially crosslinked. In a further aspect of the invention, the drug-eluting stent comprising at least one drug-loaded collagen layer that is at least partially crosslinked may further comprise at least one drug-containing biodegradable polymer layer. In one embodiment, the collagen layer(s) and the biodegradable polymer layer(s) may overlap each other. In another embodiment, the collagen layer may comprise a minor component of biodegradable polymer whereas the biodegradable polymer layer may comprise a minor component of collagen, wherein the collagen may be partially crosslinked thereafter. The drug in each layer may have different total content, drug concentration, drug type or combination of drug types. As used herein, the term "biodegradable" refers to materials that are bioresorbable and/or degrade and/or break down by mechanical degradation upon interaction with a physiological environment into components that are metabolizable or excretable, over a period of time while maintaining the requisite structural integrity. In one aspect, the biodegradable polymer comprises a biodegradable linkage selected from the group consisting of ester groups, carbonate groups, amide groups, anhydride groups, and orthoester groups.

Biodegradable Sent

Figure 9:
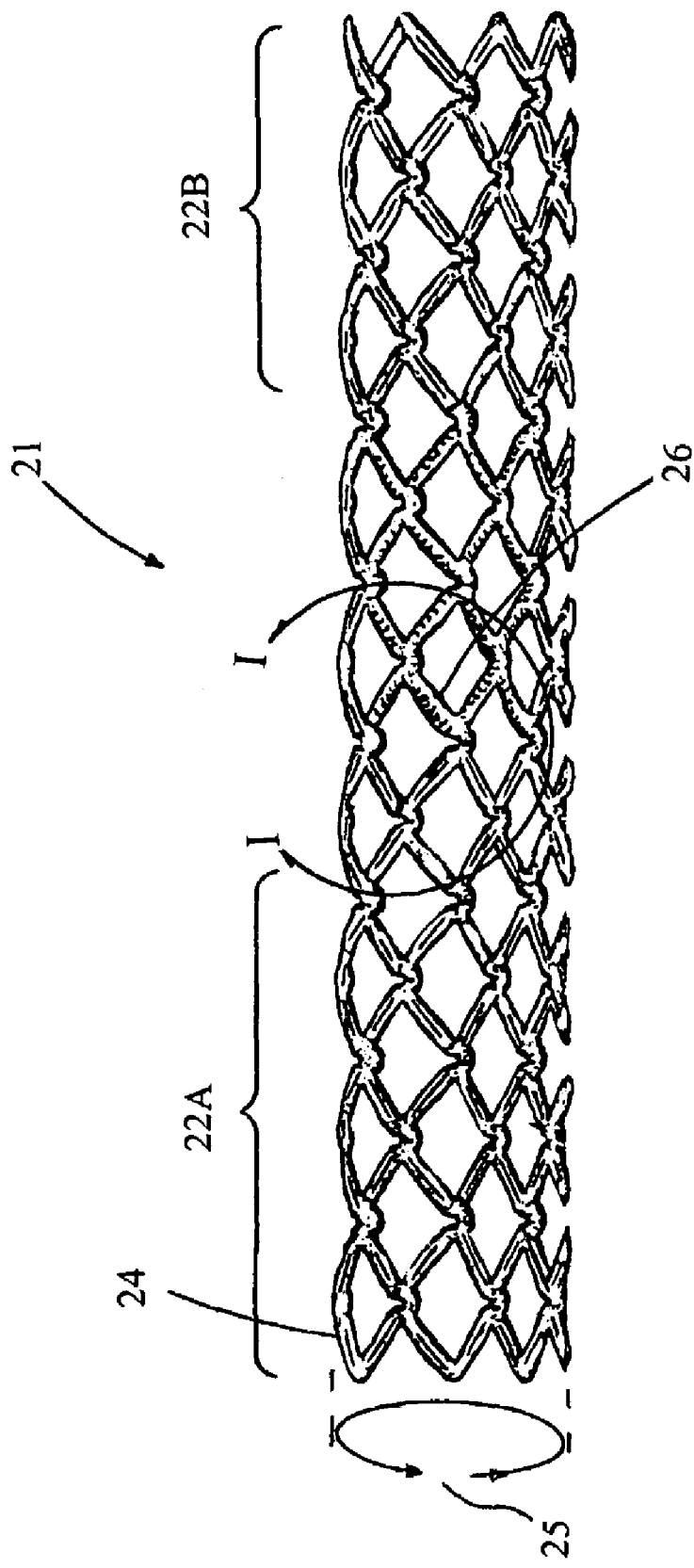
FIG. 9 is a biodegradable stent comprising a first supporting zone that comprises at least a portion of continuous circumference of the stent and a second therapeutic zone.

FIG. 9 shows one aspect of a biodegradable stent 21 for treating vulnerable plaques or target tissue of a patient comprising at least two zones, wherein a first supporting zone 22A, 22B comprises at least a portion of continuous circumference (indicated by item 25) of the stent 21, the supporting zone being made of a first biodegradable material 24; and a second therapeutic zone 23 made of a second biodegradable material 26. In another aspect of the invention, the biodegradation rate ($BR_2$) of the second biodegradable material 26 of the biodegradable stent 21 is equal to or faster than the biodegradation rate ($BR_1$) of the first biodegradable material 24. In a particular embodiment, the first biodegradable material and/or the second biodegradable material is a shape memory polymer. The charater "I" in FIG. 9 shows the interface.

U.S. Pat. Nos. 6,160,084, 6,388,043, U.S. Patent Application publication no. 2003/0055198, and no. 2004/0015187, entire contents of which are incorporated herein by reference, disclose biodegradable shape memory polymer compositions and articles manufactured therefrom. The compositions include at least one hard segment and at least one soft segment. At least one of the hard or soft segments can contain a crosslinkable group, and the segments can be linked by formation of an interpenetrating network or a semi-interpenetrating network, or by physical interactions of the segments. Objects can be formed into a given shape at a temperature above the transition temperature of the hard segment, and cooled to a temperature below the transition temperature of the soft segment. If the object is subsequently formed into a second shape, the object can return to its original shape by heating the object above the transition temperature of the soft segment and below the transition temperature of the hard segment.

Figure 10:
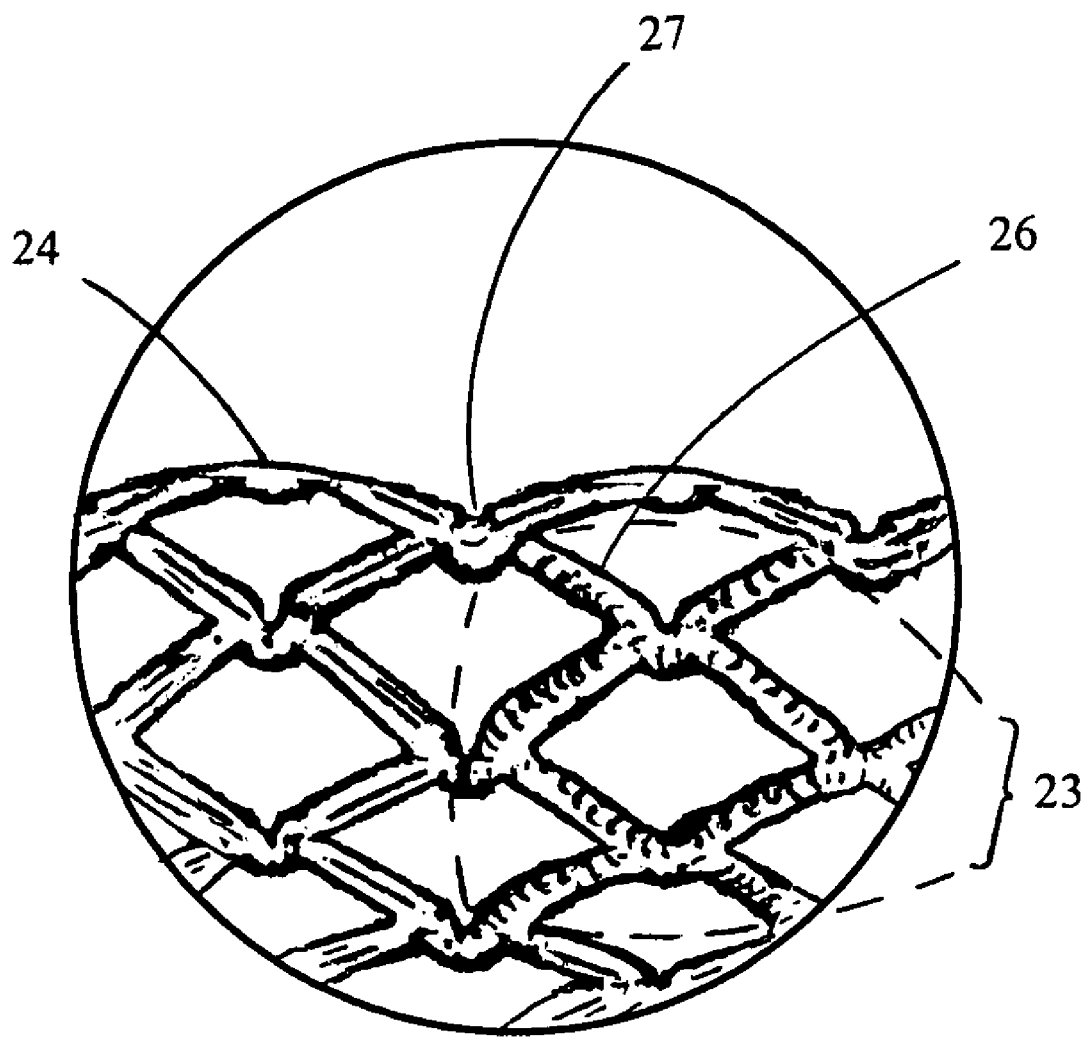
FIG. 10 is an enlarged view of the biodegradable stent, section I-I of FIG. 9, showing the interface of the first supporting zone and the second therapeutic zone.

FIG. 10 shows an enlarged view of the biodegradable stent, section I-I of FIG. 9, showing the interface 27 of the first supporting zone 22A and the second therapeutic zone 23. Particularly, the strut of the second biodegradable material 26 meets the strut of the first biodegradable material 24 at the interface 27. In the case that the biodegradation rate for the second biodegradable material ($BR_2$) is faster than the biodegradation rate of the first biodegradable material ($BR_1$), the material in the therapeutic zone will biodegrade sooner than the material in the supporting zone. Therefore, during the biodegradation period for the second biodegradable material in the therapeutic zone, the material in the supporting zone still provides appropriate structure integrity for keeping the stent in place. In one aspect, the therapeutic zone may be an isolated island surrounding by the supporting zone. In another aspect, the therapeutic zone can be a part of the continuous circumference of the stent or comprise more than one isolated island.

Figure 11:
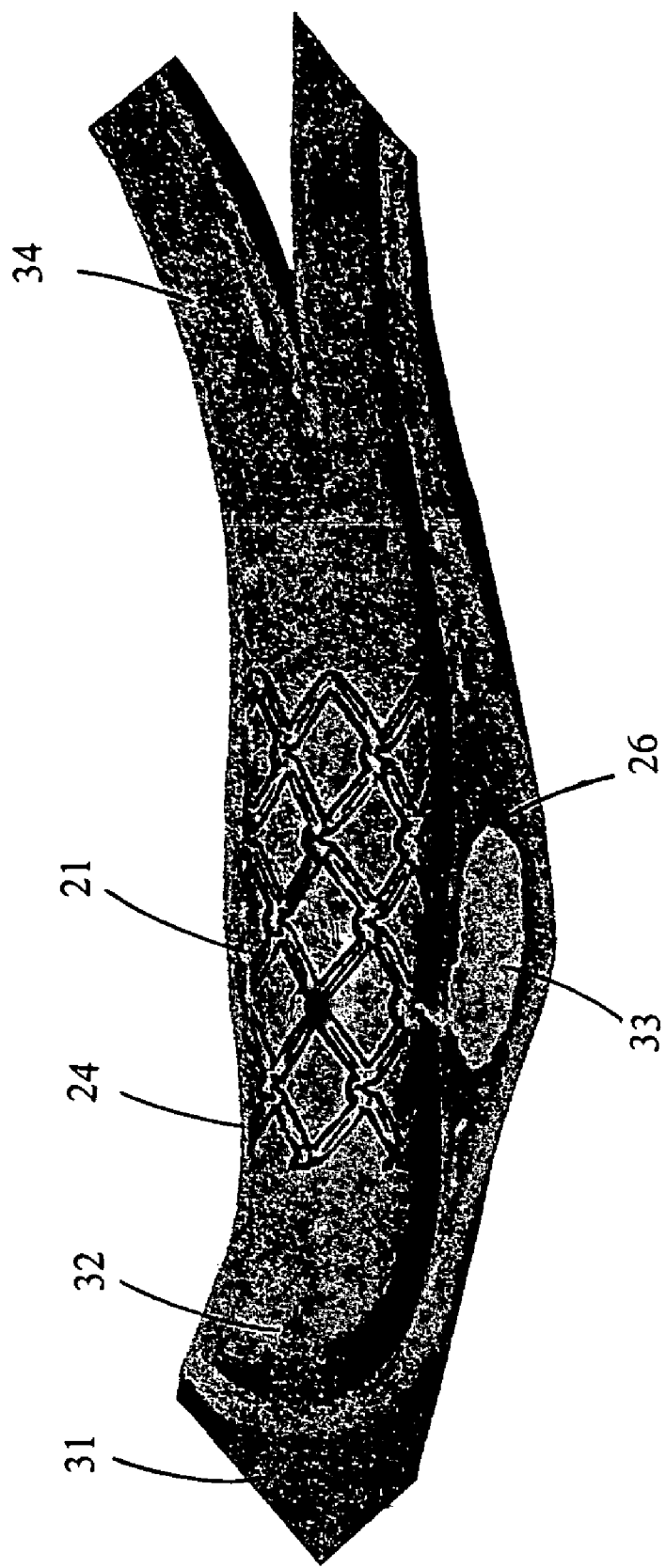
FIG. 11 is a perspective view of placing the biodegradable stent of the invention at the vulnerable plaque of a patient.

FIG. 11 shows a perspective view of placing the biodegradable stent 21 of the invention at the vulnerable plaque of a patient. The blood vessel 31 of the patient might have some bifurcation 34 and a lipid rich vulnerable plaque 33. Some aspect of the invention provides a method for treating vulnerable plaques of a patient, comprising: (a) providing a biodegradable stent 21 comprising a first supporting zone made of a first biodegradable material 24, wherein the supporting zone comprises at least a portion of continuous circumference of the stent; and a second therapeutic zone made of a second biodegradable material 26, wherein the therapeutic zone comprises at least one bioactive agent; (b) delivering the biodegradable stent to the vulnerable plaques in the lumen 32 of the blood vessel 31; (c) orienting the therapeutic zone at about the luminal surface of the vulnerable plaque 33; and (d) releasing the at least one bioactive agent for treating the vulnerable plaques. In one aspect, the therapeutic zone is capable of covering and treating more than one vulnerable plaque.

Igaki and Tamai et al. in U.S. Pat. Nos. 5,733,327, 6,045,568, and 6,080,177, entire contents of which are incorporated herein by reference, disclose luminal stents having a holding structure made of knitted yarns of biodegradable polymer fibers that subsequently disappear by being absorbed into the living tissue. Further, Igaki in U.S. Pat. Nos. 6,200,335 and 6,632,242, entire contents of which are incorporated herein by reference, discloses a stent having a main mid portion and low tenacity portions formed integrally with both ends of the main mid portion. These low tenacity portions are formed so as to have the Young's modulus approximate to that of the vessel of the living body in which is inserted the stent, so that, when the stent is inserted into the vessel, it is possible to prevent stress concentrated portions from being produced in the vessel.

In one aspect, the first biodegradable material or the second biodegradable material of the therapeutic zone of the biodegradable stent of the invention further comprises a biological material, wherein the biological material is crosslinked with a crosslinking agent or with ultraviolet irradiation. In one embodiment, the crosslinking agent is genipin, its analog, derivatives, and combination thereof. In another embodiment, the crosslinking agent is selected from a group consisting of formaldehyde, glutaraldehyde, dialdehyde starch, glyceraldehydes, cyanamide, diimides, diisocyanates, dimethyl adipimidate, carbodiimide, epoxy compound, and mixture thereof. Further, the biological material may be selected from a group consisting of collagen, gelatin, elastin, chitosan, N, O, carboxylmethyl chitosan, and mixture thereof, wherein the biological material is a solidifiable substrate, and wherein the biological material is solidifiable from a phase selected from a group consisting of solution, paste, gel, suspension, colloid, and plasma.

In some aspects, the first biodegradable material or the second biodegradable material of the biodegradable stent is made of a material selected from a group consisting of polylactic acid (PLA), polyglycolic acid (PGA), poly(D,L-lactide-co-glycolide), polycaprolactone, and co-polymers thereof. In another aspect, the first biodegradable material or the second biodegradable material of the biodegradable stent is made of a material selected from a group consisting of polyhydroxy acids, polyalkanoates, polyanhydrides, polyphosphazenes, polyetheresters, polyesteramides, polyesters, and polyorthoesters.

EXAMPLE #11 (WITH ABT-578)

In one aspect, the stent as prepared in examples of the invention is made of a metal, such as stainless steel, Nitinol, shape memory metal, cobalt-chromium alloy, other cobalt containing alloy, or the like. On another aspect, the stent as prepared in examples of the invention is made of a non-metallic polymer, such as biodegradable polymer, non-biodegradable polymer, shape memory polymer, or the like. In this example, ABT-578 is used as one of the at least one bioactive agent. In a further embodiment, the ABT-578 containing layer is on the exterior tissue-contacting side, on the interior blood-contacting side, or on the entire surface of the stent. ABT-579 (manufactured by Abbott Laboratories) is a rapamycin analog.

The material in the therapeutic zone of the biodegradable stent may comprise at least one bioactive agent. In one aspect, the at least one bioactive agent is selected from a group consisting of analgesics/antipyretics, antiasthamatics, antibiotics, antidepressants, antidiabetics, antifungal agents, antihypertensive agents, anti-inflammatories, antineoplastics, antianxiety agents, immunosuppressive agents, antimigraine agents, sedatives/hypnotics, antipsychotic agents, antimanic agents, antiarrhythmics, antiarthritic agents, antigout agents, anticoagulants, thrombolytic agents, antifibrinolytic agents, antiplatelet agents and antibacterial agents, antiviral agents, antimicrobials, and anti-infectives. In another aspect, the at least one bioactive agent is selected from a group consisting of actinomycin D, paclitaxel, vincristin, methotrexate, and angiopeptin, batimastat, halofuginone, sirolimus, tacrolimus, everolimus, tranilast, dexamethasone, ABT-578 (manufactured by Abbott Laboratories), and mycophenylic acid. In still another aspect, the at least one bioactive agent is selected from a group consisting of lovastatin, thromboxane $A_2$ synthetase inhibitors, eicosapentanoic acid, ciprostene, trapidil, angiotensin convening enzyme inhibitors, aspirin, and heparin. In a further aspect, the at least one bioactive agent is selected from a group consisting of allicin, ginseng extract, flavone, *ginkgo biloba* extract, glycyrrhetinic acid, and proanthocyanides. In some aspect, the at least one bioactive agent comprises ApoA-I Milano or recombinant ApoA-I Milano/phospholipid complexes. In one aspect, the at least one bioactive agent comprises biological cells or endothelial progenitor cells. In some aspects, the at least one bioactive agent comprises lipostabil. In some aspects, the at least one bioactive agent comprises a growth factor, wherein the growth factor is selected from a group consisting of vascular endothelial growth factor, transforming growth factor-beta, insulin-like growth factor, platelet derived growth factor, fibroblast growth factor, and combination thereof.

The polymer stent can be fabricated by extrusion, molding, welding, and weaving of fibers. Its manufacturing method may include micromachining or laser machining on a polymer tubing. A preferred method for making a biodegradable stent with at least two zones can be solution molding or thermal molding, which is well known to one skilled in the art, such as exemplified in U.S. Pat. No. 6,200,335.

Suitable biodegradable polymer to be used in the prestent invention can be found in Handbook of Biodegradable Polymers by Domb et al. (Harwood Academic Publishers: Amsterdam, The Netherlands 1997). Some aspects of the invention provide, in combination, biodegradable and/or bioresorbable polymer as drug carrier and partially crosslinked collagen drug carrier in a drug-eluting stent of the prestent invention. Some aspects of the invention relate to a medical device, comprising: a biodegradable apparatus having a surface; at least one bioactive agent; and biological material loaded onto at least a portion of the surface of the apparatus, the biological material comprising the at least one bioactive agent, wherein the biological material is crosslinked with a crosslinking agent or with ultraviolet irradiation.

Suitable biodegradable polymer may comprise polylactic acid (PLA), polyglycolic acid (PGA), poly(D,L-lactide-co-glycolide), polycaprolactone, hyaluric acid, adhesive proteins, and co-polymers of these materials as well as composites and combinations thereof and combinations of other biodegradable material. Preferably the materials have been approved by the U.S. Food and Drug Administration. The differentiation of collagen from a biodegradable polymer as a drug carrier is that collagen is crosslinkable after being loaded onto a stent while the polymer is not crosslinkable any more.

One preferred aspect of the invention provides a method for treating a target tissue of a patient comprising: (a) crosslinking a biological material with a crosslinking agent; (b) mixing a bioactive agent with the biological material; (c) loading the biological material onto at least a portion of a surface of a medical device or an apparatus; and (d) delivering the medical device to the target tissue and releasing the bioactive agent for treating the target tissue. In one embodiment, the method comprises a step of solidifying the biological material before the delivering step. In another embodiment, the method further comprises a step of chemically linking the bioactive agent with the biological material through a crosslinker before the solidifying step, wherein the bioactive agent comprises at least a crosslinkable functional group.

In a broader scope of the prestent invention, the "drug" further comprises bioactive agents or materials which may be used in the prestent invention include, for example, pharmaceutically active compounds, proteins, oligonucleotides, ribozymes, anti-sense genes, DNA compacting agents, gene/vector systems (i.e., anything that allows for the uptake and expression of nucleic acids), nucleic acids (including, for example, naked DNA, cDNA, RNA, DNA, cDNA, or RNA in a non-infectious vector or in a viral vector which may have attached peptide targeting sequences; anti-sense nucleic acid (RNA or DNA); and DNA chimeras which include gene sequences and encoding for ferry proteins such as membrane translocating sequences ("MTS") and herpes simplex virus-1 ("VP22")), and viral, liposomes and cationic polymers that are selected from a number of types depending on the desired application, including retrovirus, adenovirus, adeno-associated virus, herpes simplex virus, and the like.

For example, biologically active solutes include anti-thrombogenic agents such as heparin, heparin derivatives, urokinase, PPACK (dextrophenylalanine proline arginine chloromethylketone), rapamycin, probucol, and verapamil; angiogenic and anti-angiogenic agents; anti-proliferative agents such as enoxaparin, angiopeptin, or monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, and mesalamine; anti-neoplastic/antiproliferative/anti-mitotic agents such as paclitaxel, 5-fluorouracil, cisplatin, vinblastine, vincristine, epothilones, endostatin, angiostatin and thymidine kinase inhibitors; anesthetic agents such as lidocaine, bupivacaine, and ropivacaine; anti-coagulants such as D-Phe-Arg chloromethyl keton, and RGD peptide-containing compound, heparin, antithrombin compounds, platelet receptor antagonists, anti-thrombin antibodies, antiplatelet receptor antibodies, aspirin, prostaglandin inhibitors, platelet inhibitors and tick antiplatelet factors; vascular cell growth promoters such as growth factors, growth factor receptor antagonists, transcriptional activators, and translational promoters; vascular cell growth inhibitors such as growth factor inhibitors, growth factor receptor antagonists, transcriptional repressors, translational repressors, replication inhibitors, inhibitory antibodies, antibodies directly against growth factors, bifunctional molecules consisting of a growth factor and a cytotoxin, bifunctional molecules consisting of an antibody and a cytotoxin; cholesterol-lowering agents; vasodilating agents; agents which interfere with endogenous vasoactive mechanisms, and combinations thereof. These and other compounds are applicable to the device and methods of the invention.

U.S. Pat. No. 6,423,682, issued on Jul. 23, 2002 and U.S. Pat. No. 6,485,920, issued on Nov. 26, 2002, the entire contents of both of which are incorporated herein by reference, disclose the compositions of novel human growth factor antagonist proteins and active variants thereof, isolated polynucleotides encoding such polypeptides, including recombinant DNA molecules, cloned genes or degenerate variants thereof, especially naturally occurring variants such as allelic variants, antisense polynucleotide molecules, and antibodies that specifically recognize one or more epitopes prestent on such polypeptides, as well as hybridomas producing such antibodies function of mitochondria and toxic substances synthesized as a metabolic byproduct within mitochondria of cells. Some aspects of the prestent invention provide a device comprising solidifiable bioactive agent-containing biological material loaded onto at least a portion of the surface of the device, followed by being crosslinked with a crosslinking agent, wherein the bioactive agent comprises at least one of the above-cited genes.

U.S. Pat. No. 6,476,211, issued on Nov. 5, 2002, the entire contents of which are incorporated herein by reference, discloses human CD39-like protein polynucleotides isolated from cDNA libraries of human fetal liver-spleen and macrophage as well as polypeptides encoded by these polynucleotides and mutants or variants thereof. CD39 (cluster of differentiation 39) is a cell-surface molecule recognized by a "cluster" of monoclonal antibodies that can be used to identify the lineage or stage of differentiation of lymphocytes and thus to distinguish one class of lymphocytes from another. Some aspects of the prestent invention provide a device comprising solidifiable bioactive agent-containing biological material loaded onto at least a portion of the surface of the device, followed by being crosslinked with a crosslinking agent, wherein the bioactive agent comprises the above-cited human CD39-like protein polynucleotides or the like.

U.S. Pat. No. 5,780,052, issued Jul. 14, 1998, the entire contents of which are incorporated herein by reference, discloses a method of salvaging a target cell from cell death, comprising contacting a target cell having a disrupted cell membrane with a specific affinity reagent-liposome conjugate in an amount effective and for a time sufficient to allow the conjugate to prevent cell death due to membrane disruption. The patent discloses methods of delivering a selected agent into a damaged target cell for diagnosis and therapy, wherein the conjugate comprises a biological agent selected from the group consisting of fibroblastic growth factor-β, angiogenic factors, high energy substrates for the myocardium, antioxidants, cytokines and contrast agents. Some aspects of the prestent invention provide a device comprising solidifiable bioactive agent-containing biological material loaded onto at least a portion of the surface of the device, followed by being crosslinked with a crosslinking agent, wherein the bioactive agent comprises the above-cited fibroblastic growth factor-β, angiogenic factors, high energy substrates for the myocardium, antioxidants, cytokines and the like.

U.S. Pat. No. 6,475,784, issued on Nov. 5, 2002, the entire contents of which are incorporated herein by reference, discloses a method for polypeptides having anti-angiogenic activity and nucleic acids that encode these polypeptides. The anti-angiogenic polypeptides include at least kringles 1-3 of plasminogen. The patent '784 also provides methods of using the polypeptides and nucleic acids for inhibiting angiogenesis and other conditions characterized by undesirable endothelial cell proliferation. Angiostatin, which is an angiogenesis inhibitor, is a naturally occurring internal cleavage product of plasminogen, wherein human plasminogen has five characteristic protein domains called "kringle structures". Some aspects of the prestent invention provide a device comprising solidifiable bioactive agent-containing biological material loaded onto at least a portion of the surface of the device, followed by being crosslinked with a crosslinking agent, wherein the bioactive agent comprises the above-cited anti-angiogenic polypeptides, angiostatin, angiogenesis inhibitor, and the like.

U.S. Pat. No. 6,436,703, issued on Aug. 20, 2002, the entire contents of which are incorporated herein by reference, discloses a method and compositions comprising novel isolated polypeptides, novel isolated polynucleotides encoding such polypeptides, including recombinant DNA molecules, cloned genes or degenerate variants thereof, especially naturally occurring variants such as allelic variants, antisense polynucleotide molecules, and antibodies that specifically recognize one or more epitopes present on such polypeptides, as well as hybridomas producing such antibodies. The compositions in '703 additionally include vectors, including expression vectors, containing the polynucleotides of the invention, cells genetically engineered to contain such polynucleotides and cells genetically engineered to express such polynucleotides. Some aspects of the prestent invention provide a device comprising solidifiable bioactive agent-containing biological material loaded onto at least a portion of the surface of the device, followed by being crosslinked with a crosslinking agent, wherein the bioactive agent comprises the above-cited antisense polynucleotide molecules and the like.

U.S. Pat. No. 6,451,764, issued on Sep. 17, 2002, the entire contents of which are incorporated herein by reference, discloses a method of treating vascular tissue and promoting angiogenesis in a mammal comprising administering to the mammal an effective amount of the composition comprising VRP (vascular endothelial growth factor-related protein). The disclosure '764 further provides a method for treating trauma affecting the vascular endothelium comprising administering to a mammal suffering from the trauma an effective amount of the composition containing the VRP, or a method for treating a dysfunctional state characterized by lack of activation or lack of inhibition of a receptor for VRP in a mammal. Some aspects of the prestent invention provide a device comprising solidifiable bioactive agent-containing biological material loaded onto at least a portion of the surface of the device, followed by being crosslinked with a crosslinking agent, wherein the bioactive agent comprises the above-cited inhibitors or receptors for vascular endothelial growth factor-related protein and the like.

It was reported in *JAMA*. 2003; 290:2292-2300 and 2322-2324, entire contents of which are incorporated herein by reference, that infusion of Milano Apoprotein causes rapid regression of atherosclerosis in patients with acute coronary syndromes (ACS), according to the results of a preliminary randomized trial published in the November 5 issue of The Journal of the American Medical Association. This intravenous therapy targeting high-density lipoprotein cholesterol (HDL-C) may represent a new approach to the future treatment of atherosclerosis. "Approximately 40 carriers with a naturally occurring variant of apolipoprotein A-I known as ApoA-I Milano are characterized by very low levels of HDL-C, apparent longevity, and much less atherosclerosis than expected for their HDL-C levels," write Steven E. Nissen, MD, from the Cleveland Clinic Foundation in Ohio, and colleagues. Of 123 patients with ACS, aged 38 to 82 years, who were screened between November 2001 and March 2003 at 10 U.S. centers, 57 patients were randomized. Of 47 patients who completed the protocol, 11 received placebo, 21 received low-dose and 15 received high-dose recombinant ApoA-I Milano/phospholipid complexes (ETC-216) by intravenous infusion at weekly intervals for five doses. Serial intravascular ultrasound measurements within two weeks of ACS and after treatment revealed that the mean percentage of atheroma volume decreased by 1.06% in the combined ETC-216 group compared with an increase of 0.14% in the placebo group. In the combined treatment groups, the absolute reduction in atheroma volume was a 4.2% decrease from baseline.

This initial trial of an exogenously produced HDL mimetic demonstrated significant evidence of rapid regression of atherosclerosis. The authors write, "the potential utility of the new approach must be fully explored in a larger patient population with longer follow-up, assessing a variety of clinical end points, including morbidity and mortality". In an accompanying editorial, Daniel J. Rader, MD, from the University of Pennsylvania School of Medicine in Philadelphia, discusses several study limitations, including small sample size, short treatment duration, unclear relationship of intravascular ultrasound findings to clinical benefit, and failure to compare infusion of normal ApoA-I with that of ApoA-I Milano.

The mechanisms of action of ApoA-I Milano and phospholipid complex that result in regression of atherosclerosis are unknown but presumably are related to an increase in reverse cholesterol transport from atheromatous lesions to the serum with subsequent modification and removal by the liver (*JAMA*. 2003; 290:2292-2300). The cysteine substitution for arginine at position 173 for the ApoA-I Milano variant allows dimerization, forming large HDL particles that may be particularly active in reverse cholesterol transport. In vitro experiments have demonstrated increased cholesterol efflux from cholesterol-loaded hepatoma cells incubated with serum from ApoA-I Milano carriers or from transgenic mice. As a result, some day patients with acute coronary syndromes may receive 'acute induction therapy' with HDL-based therapies for rapid regression and stabilization of lesions, followed by long-term therapy to prevent the regrowth of these lesions. In this model, long-term HDL-based therapies will still be needed as a vital component of the preventive phase.

The bioactive agent of the present invention further comprises ApoA-I Milano, recombinant ApoA-I Milano/phospholipid complexes (ETC-216), and the like in treating atherosclerosis, both stenotic plaque and vulnerable plaque of a patient for regression and stabilization of lesions. Some aspects of the invention relate to a drug-eluting stent, comprising a biodegradable or non biodegradable stent base coated with at least one layer of partially crosslinked biological material (for example, collagen). In one embodiment, the at least one biological material layer comprises ApoA-I Milano or recombinant ApoA-I Milano/phospholipid complexes. In another embodiment, the at least one biological material layer comprises ApoA-I Milano, recombinant ApoA-I Milano/phospholipid complexes, and other bioactive agent(s). In still another embodiment, a drug-eluting stent of the invention comprises a biodegradable or non biodegradable stent base coated with at least one layer of biodegradable polymer (or combination of biodegradable polymer and partially crosslinked biological material, such as collagen) that is loaded with ApoA-I Milano, or recombinant ApoA-I Milano/phospholipid complexes. In one preferred embodiment, a biodegradable medical device or a biodegradable drug-eluting stent of the invention comprising at least one bioactive agent selected from a group consisting of ApoA-I Milano, recombinant ApoA-I Milano/phospholipid complexes, lipostabil, and combination thereof.

EXAMPLE #12

In one aspect, the stent as prepared in examples of the invention is made of a material selected from a group consisting of stainless steel, Nitinol, cobalt-chromium alloy, other cobalt containing alloy, shape memory metal, biodegradable polymer, non-biodegradable polymer, shape memory polymer, or the like. In this example, the stent from either Example 9 or 10 is further coated with PC (phosphorylcholine). In a further embodiment, the PC coating is at least on the inner surface (that is, the blood contacting side after implanted in a blood vessel) of the stent. In another embodiment, the PC coating is at least on the outer surface (that is, the tissue contacting side after implanted in a blood vessel) of the stent. In still another embodiment, the PC coating is over the entire surface of the stent.

PC is found in the inner and outer layers of cell membrane. However, it is the predominant component present in the outer membrane layer, and because it carries both a positive and negative charge (zwitterionic), it is electrically neutral. As a result, the outer layer of the cell membrane does not promote clot formation. When PC is coated on or incorporated on a material, protein and cell adhesion is decreased, clot formation is minimized, inflammatory response is lessened, and fibrous capsule formation is minimized. Some aspects of the invention relate to a drug-eluting stent comprising an immobilized antibody (such as CD34 or the like) that attracts endothelial progenitor cells from the circulating blood stream, resulting in endothelial coverage over and between the stent struts. In a further embodiment, the antibody loading is at least on the inner surface, at least on the outer surface, or over the entire surface of the stent.

From the foregoing description, it should now be appreciated that a novel and unobvious process for making a biological substance comprising an illustrative collagen-drug-genipin compound or chitosan-drug-genipin compound for drug slow release has been disclosed for tissue treatment applications. The process comprises, in combination, mixing a drug with a solidifiable biological material, chemically treating the biological material and/or the drug with a crosslinking agent, loading the solidifiable drug-containing biological material onto a medical device, and solidifying the drug-containing biological material. The resulting biological substance is generally characterized with reduced antigenicity, reduced immunogenicity, and reduced enzymatic degradation and capable of drug slow-release. While the invention has been described with reference to a specific embodiment, the description is illustrative of the invention and is not to be construed as limiting the invention. Various modifications and applications may occur to those who are skilled in the art, without departing from the true spirit and scope of the invention.

What is claimed is:

1. A biodegradable stent for treating vulnerable plaques or atherosclerotic plaques of a patient comprising:
   at least two zones, wherein a first supporting zone comprises a first biodegradable material;
   a second therapeutic zone comprising a second biodegradable material, wherein at least one of the first and the second biodegradable material comprises at least one bioactive agent and wherein the at least one bioactive agent comprises lipostabil.

2. A biodegradable stent for treating vulnerable plaques or atherosclerotic plaques of a patient comprising:
   at least two zones, wherein a first supporting zone comprises a first biodegradable material;
   a second therapeutic zone comprising a second biodegradable material, wherein at least one of the first and the second biodegradable material further comprises a biological material, wherein said biological material is crosslinked with a crosslinking agent or with ultraviolet irradiation; and
   wherein the crosslinking agent is genipin, its analog, derivatives, and combination thereof.

3. The stent according to claim 2, wherein said biological material is selected from the group consisting of collagen, gelatin, elastin, chitosan, N, O, carboxylmethyl chitosan, and mixture thereof.

4. The stent according to claim 2, wherein at least one of the first and the second biodegradable material is a shape memory polymer.

5. The stent according to claim 2, wherein at least one of the first and the second biodegradable material comprises at least one bioactive agent.

6. The stent according to claim 2, wherein at least one of the first and the second biodegradable material comprises at least one bioactive agent and wherein the at least one bioactive agent comprises lipostabil.

7. The stent according to claim 2, wherein at least one of the first and the second biodegradable material comprises at least one bioactive agent and wherein the at least one bioactive agent comprises analgesics/antipyretics.

8. The stent according to claim 2, wherein at least one of the first and the second biodegradable material comprises at least one bioactive agent and wherein the at least one bioactive agent comprises ApoA-I Milano or recombinant ApoA-I Milano/phospholipid complexes.

9. The stent according to claim 2, wherein at least one of the first and the second biodegradable material comprises at least one bioactive agent and wherein the at least one bioactive agent comprises a growth factor.

10. The stent according to claim 2, wherein at least one of the first and the second biodegradable material comprises at least one bioactive agent and wherein the at least one bioactive agent comprises everolimus.

11. The stent according to claim 2, wherein at least one of the first and the second biodegradable material comprises at least one bioactive agent and wherein the at least one bioactive agent comprises angiotensin convening enzyme inhibitors.

12. The stent according to claim 2, wherein at least one of the first and the second biodegradable material comprises at least one bioactive agent and wherein the at least one bioactive agent comprises endothelial progenitor cells.

* * * * *